(12) United States Patent
Dooley et al.

(10) Patent No.: US 12,296,282 B2
(45) Date of Patent: May 13, 2025

(54) SYSTEM AND METHOD FOR EXTRACTING AND SEPARATING BOTANICAL OILS WITHOUT THE USE OF SOLVENTS

(71) Applicant: Botanical Extraction Solvent Free Ltd., Zurich (CA)

(72) Inventors: Kevin Allan Dooley, Zurich (CA); Elwood A. Morris, Nanaimo (CA); Joshua David Bell, Long River (CA); Adam Charles Dooley, Wasaga Beach (CA)

(73) Assignee: Botanical Extraction Solvent Free Ltd., Zurich (CA)

( * ) Notice: Subject to any disclaimer, the term of this patent is extended or adjusted under 35 U.S.C. 154(b) by 0 days.

(21) Appl. No.: 18/449,057

(22) Filed: Aug. 14, 2023

(65) Prior Publication Data
US 2023/0381685 A1    Nov. 30, 2023

Related U.S. Application Data

(63) Continuation of application No. 16/448,745, filed on Jun. 21, 2019, now Pat. No. 12,064,710, which is a (Continued)

(30) Foreign Application Priority Data

May 30, 2018    (CA) ................................ CA 3006692

(51) Int. Cl.
*B01D 11/02*    (2006.01)
*B01D 11/00*    (2006.01)
(Continued)

(52) U.S. Cl.
CPC ...... *B01D 11/0211* (2013.01); *B01D 11/0207* (2013.01); *B01D 11/028* (2013.01);
(Continued)

(58) Field of Classification Search
CPC .... B03C 3/15; B03C 3/10; B03C 3/41; B03C 3/45; B03C 3/017; B03C 3/38;
(Continued)

(56) References Cited

U.S. PATENT DOCUMENTS 5,591,253 A * 1/1997 Altman ..................... B04C 5/04
96/61
7,527,675 B2 * 5/2009 Bertuccioli ............... B03C 3/15
96/99
(Continued)

FOREIGN PATENT DOCUMENTS

JP      2000126650 A  *  5/2000  ............... B03C 7/06
WO  WO-2017192527 A1 * 11/2017  ............... B01D 1/14

*Primary Examiner* — Christopher P Jones
*Assistant Examiner* — Sonji Turner
(74) *Attorney, Agent, or Firm* — Smart & Biggar LP

(57) ABSTRACT

A system and method for extracting and separating botanical oils and compounds from botanical material without the use of solvents, having a vaporizing section which is further coupled to a centrifugal electrostatic precipitator for collection and segregation. The vaporizing section receives the botanical material through which a temperature-controlled inert gas is passed to evaporate specific vaporization temperature oils or compounds from the botanical material. The extracted vapor passes to the centrifugal electrostatic precipitator where the oil or compound is reduced back to the liquid state and is collected and segregated. The oils having the lower vapor temperature are collected first and the remaining oils are collected by specific and progressive vaporization temperature control. In some examples, selected vaporized compounds are waste exhausted as vapor by bypassing the centrifugal electrostatic precipitator at specific known vapor temperatures, thereby eliminating potentially toxic or undesirable oils or compounds from being collected.

29 Claims, 16 Drawing Sheets

Related U.S. Application Data continuation-in-part of application No. PCT/CA2019/050231, filed on Feb. 27, 2019.

(51) Int. Cl.

| | |
|---|---|
| *B03C 3/017* | (2006.01) |
| *B03C 3/10* | (2006.01) |
| *B03C 3/15* | (2006.01) |
| *B03C 3/38* | (2006.01) |
| *B03C 3/41* | (2006.01) |
| *B03C 3/49* | (2006.01) |
| *C07D 311/80* | (2006.01) |

(52) U.S. Cl.
CPC ................ *B03C 3/017* (2013.01); *B03C 3/10* (2013.01); *B03C 3/15* (2013.01); *B03C 3/38* (2013.01); *B03C 3/41* (2013.01); *B03C 3/49* (2013.01); *C07D 311/80* (2013.01); *B01D 2011/007* (2013.01)

(58) Field of Classification Search
CPC ....... B03C 3/49; B03C 3/011; B01D 11/0211; B01D 11/0207; B01D 11/028; B01D 2011/007; B01D 5/006; B01D 5/0027; B01D 45/12; B07B 7/08; C07D 311/80; C11B 3/00; C11B 3/006; C11B 9/027; C11B 1/10; A23D 9/02; A61K 36/185; A61K 36/348; A61K 36/3482; A61K 36/3486; A61K 36/577; A61K 36/5775; A61K 36/5777; A61K 36/742; A61K 2236/00; A61K 36/30

See application file for complete search history.

(56) References Cited

U.S. PATENT DOCUMENTS

| | | | | |
|---|---|---|---|---|
| 8,029,601 | B2 * | 10/2011 | Franzen | .................... B04B 5/10 |
| | | | | 96/61 |
| 2010/0119606 | A1 * | 5/2010 | Whittle | ................ A61K 36/185 |
| | | | | 424/484 |
| 2017/0202896 | A1 * | 7/2017 | Hugh | .................... A23L 33/105 |
| 2018/0029043 | A1 * | 2/2018 | Henriquez Prevoo | .... B03C 3/78 |
| 2018/0078874 | A1 * | 3/2018 | Thomas | ................. B01D 53/18 |

* cited by examiner

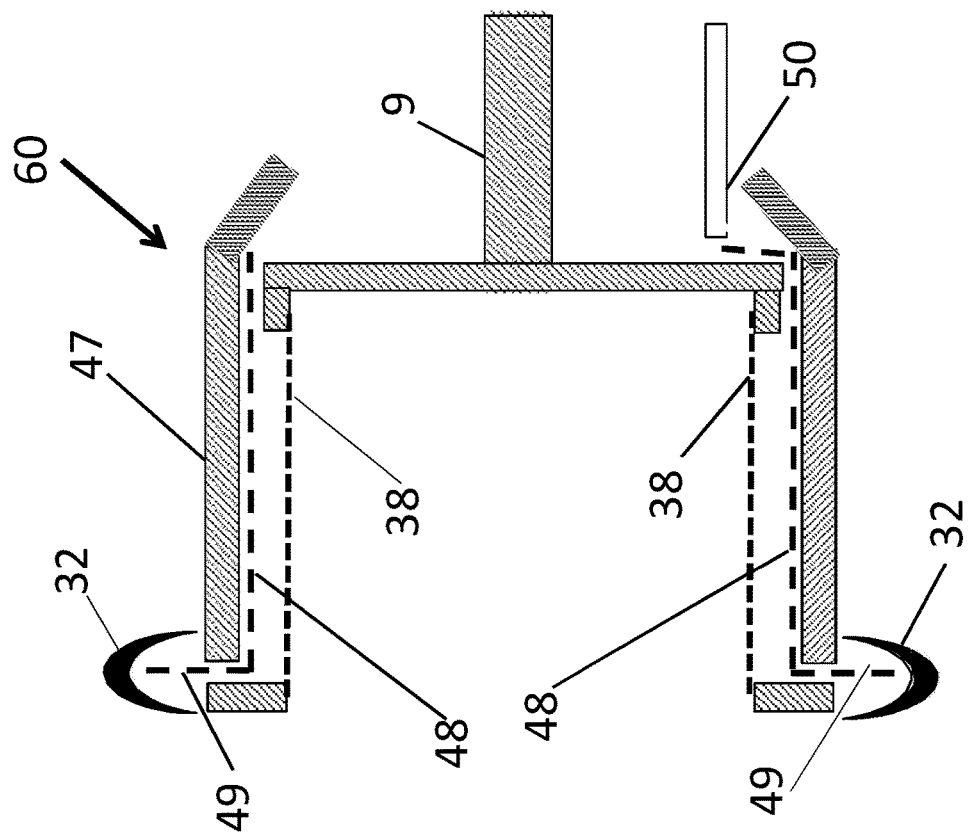
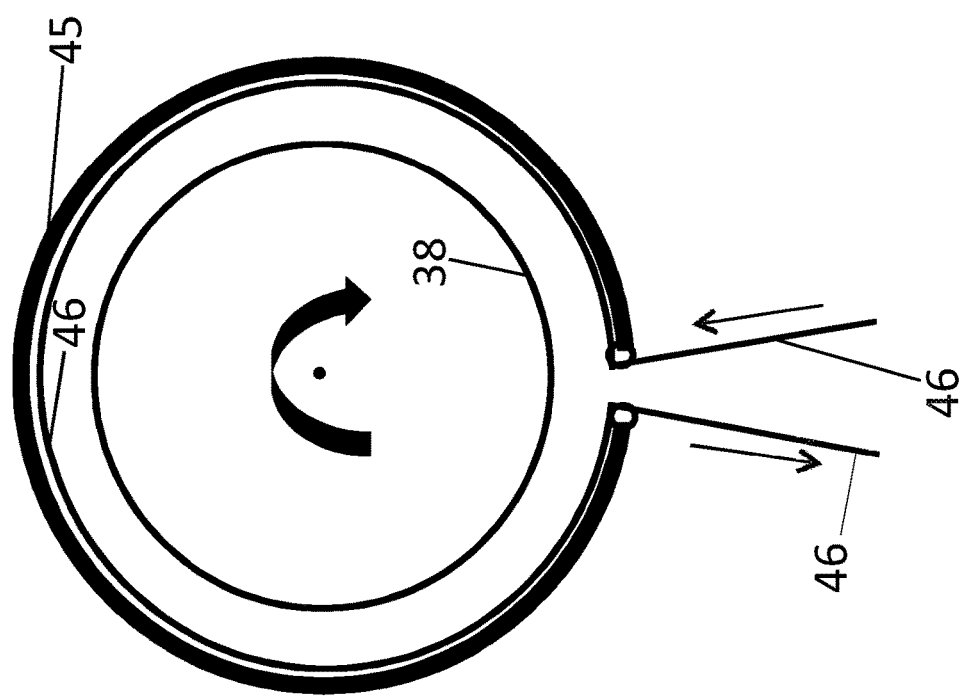
Figure 6
Figure 5

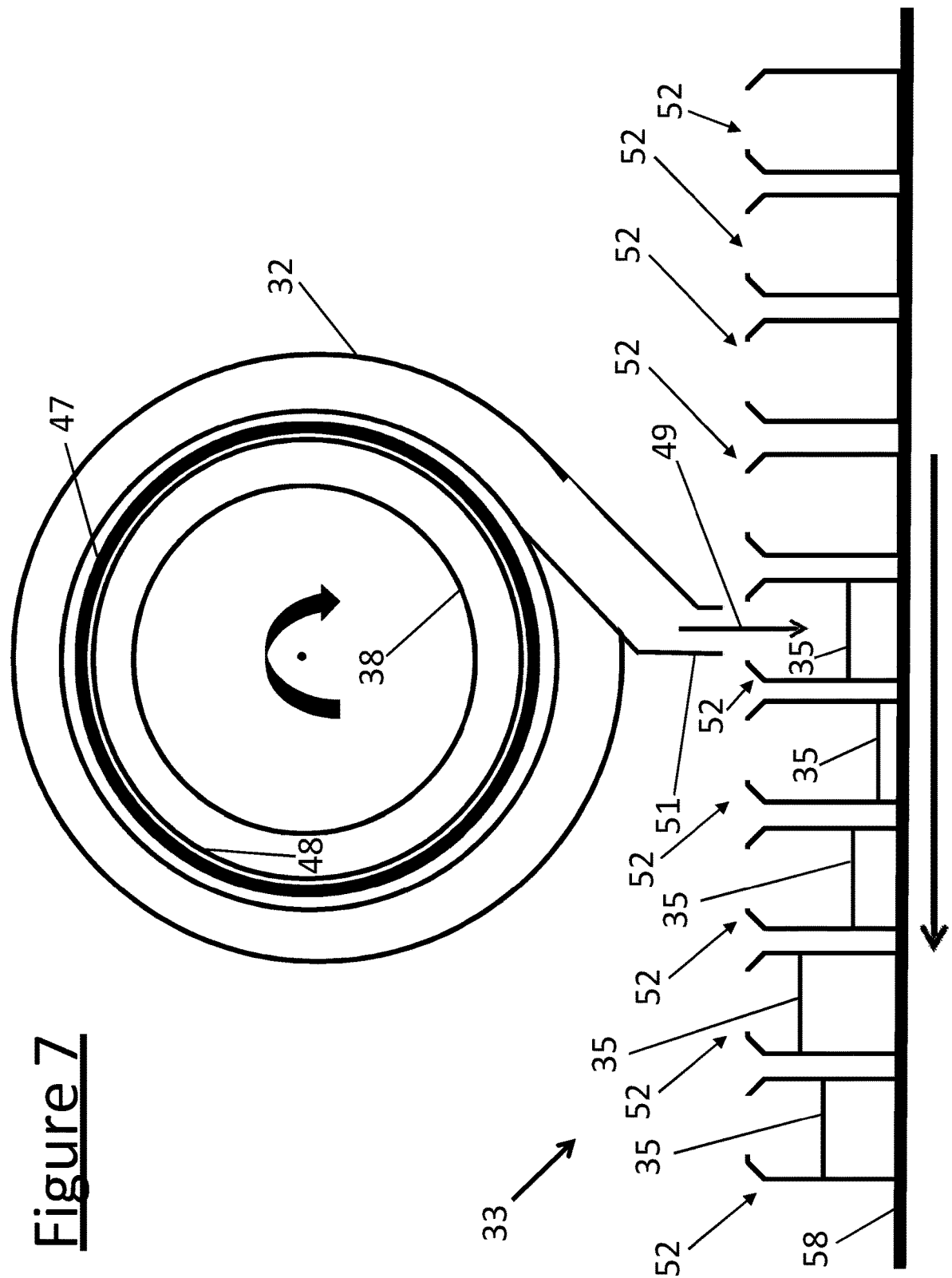

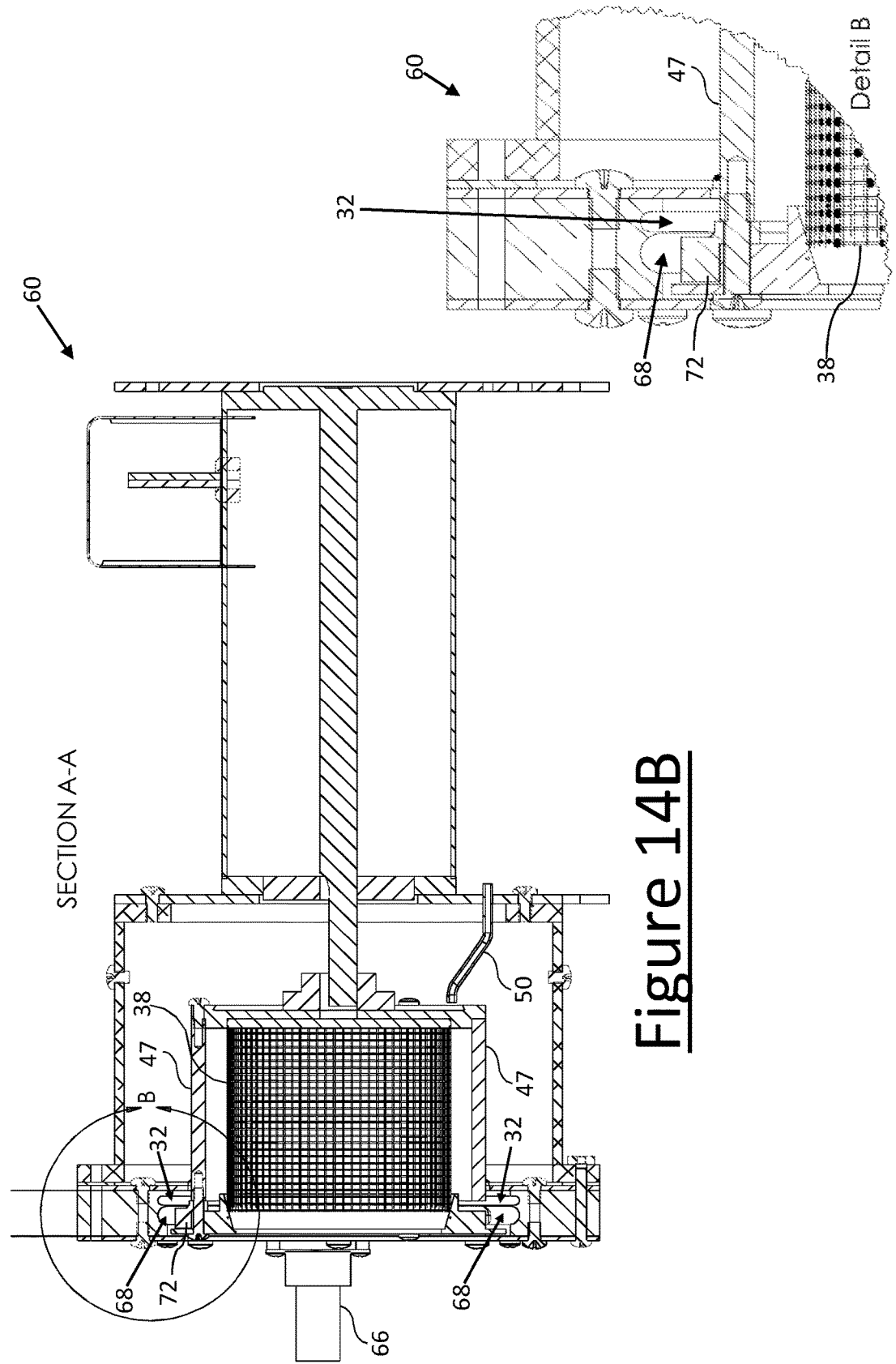

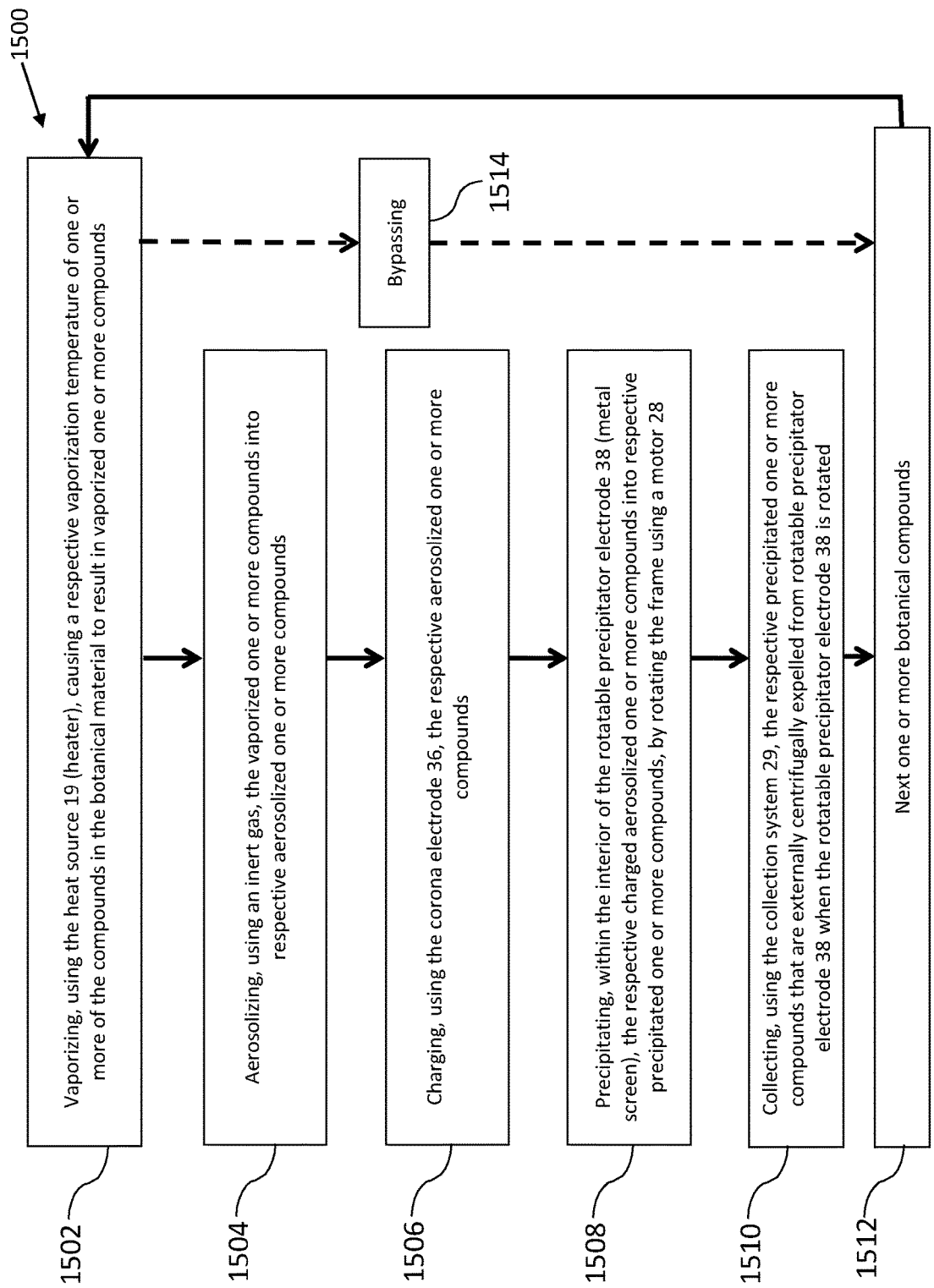

SYSTEM AND METHOD FOR EXTRACTING AND SEPARATING BOTANICAL OILS WITHOUT THE USE OF SOLVENTS

CROSS REFERENCE TO RELATED APPLICATION(S)

This application is a Continuation Application of U.S. application Ser. No. 16/448,745, filed Jun. 21, 2019 and entitled "SYSTEM AND METHOD FOR EXTRACTING AND SEPARATING BOTANICAL OILS WITHOUT THE USE OF SOLVENTS", which is a Continuation-In-Part Application of PCT Patent Application Serial No. PCT/CA2019/050231, filed Mar. 4, 2019 and entitled "SYSTEM AND METHOD FOR EXTRACTING AND SEPARATING BOTANICAL OILS WITHOUT THE USE OF SOLVENTS", which claims the benefit of priority to Canadian Patent Application Serial Number 3006692, filed May 30, 2018 and entitled "A SYSTEM AND METHOD FOR EXTRACTING AND SEPARATING BOTANICALS OILS WITHOUT THE USE OF SOLVENTS", the entire contents of these applications are herein incorporated by reference into the Detailed Description of Example Embodiments, herein below.

TECHNICAL FIELD

Example embodiments relate to extraction and separation of botanical oils and other compounds from plant material.

BACKGROUND

Botanical oils are presently extracted from plant materials (botanical materials); in general through the use of pressing or through some form of liquid solvent to dissolve and mobilize the oils to liberate them from the plant material. The solvents are later removed from the oils by evaporation or vacuum distillation techniques. Traces of some solvents may remain as a contaminant in the oil or compound, which may be detrimental or may restrict applications of the extracted oils or compounds, particularly if the oil or compound is intended for consumption such as for medicinal purposes, cosmetic purposes or recreational purposes.

In many of these solvent type processes, a broad spectrum mixture often results which may require further separation or fractionation processing to remove or segregate the various oils and compounds for different purposes applications or effects.

An example of such botanical extraction may be performed on *cannabis* botanical material. Solvent methods of liberating oils and other compounds from the *cannabis* botanical material tend to dissolve any and all oils and other compounds within the plant material, and the resulting broad spectrum product generally requires further fractional distillation processing to separate undesirable oils or compounds and solvent from the desired products before the extract can be used for its intended purpose. Different oils and compounds found in the same plant material may have widely differing and varying uses once separated. Some compounds may be considered toxic under certain conditions potentially limiting the applicability of certain extracts.

It may be advantageous to provide improved and efficient systems and methods for the harvesting of specific botanical oils and compounds from plant materials without the use of potentially contaminating solvents during vaporization or using conventional fractional distillation systems.

Additional difficulties with existing systems may be appreciated in view of the Detailed Description of Example Embodiments, herein below.

SUMMARY

Example embodiments relate to a system and method for the extraction and separation of botanical oils and other compounds from botanical material, for example for the purpose of extracting and separating multiple and various oils and other compounds from *cannabis* botanical material without the use of solvents or a conventional fractional distillation technique.

In an example embodiment, there is provided a system and a method for extracting and separating botanical oils and other compounds from botanical material comprising several oil or other compound types. The system and method can also be useful with other broad-spectrum compounds where practical, where it may be more convenient than conventional fractional distillation techniques.

According to an example embodiment, there is provided a system for extracting compounds from botanical material, comprising: a heater for sequentially vaporizing the botanical material at specified temperature values, each specified temperature value causing a respective vaporization temperature of one or more of the compounds in the botanical material to result in respective vaporized one or more compounds; a gas inlet for receiving an inert gas, the inert gas being for sequentially aerosolizing each of the respective vaporized one or more compounds into respective aerosolized one or more compounds; a corona electrode for sequentially charging each of the respective aerosolized one or more compounds; an electrostatic precipitator including a frame having a metal screen and the metal screen defines an interior for receiving and sequentially precipitating each of the respective charged aerosolized one or more compounds into respective precipitated one or more compounds, a motor for controlling rotation the frame having the metal screen around an axis of rotation to perform said precipitating; and a collection system at least part of which is positioned radially exterior from the frame having the metal screen with respect to the axis of rotation, the collection system for sequentially collecting each of the respective precipitated one or more compounds for each specified temperature value that are externally centrifugally expelled from the frame having the metal screen when the frame is rotated.

An example embodiment is method for extracting compounds from botanical material, comprising: sequentially vaporizing, using a heater, the botanical material at specified temperature values, each specified temperature value causing a respective vaporization temperature of one or more of the compounds in the botanical material to result in respective vaporized one or more compounds; for each of the vaporized one or more compounds from each specified temperature value: aerosolizing, using an inert gas, the respective vaporized one or more compounds into respective aerosolized one or more compounds, charging, using a corona electrode, the respective aerosolized one or more compounds, precipitating, within an interior of a metal screen of a frame, the respective charged aerosolized one or more compounds into respective precipitated one or more compounds, by rotating the frame using a motor, and collecting the respective precipitated one or more compounds that are externally centrifugally expelled from the frame having the metal screen when the frame is rotated.

BRIEF DESCRIPTION OF THE DRAWINGS

Reference will now be made, by way of example, to the accompanying drawings which show example embodiments, and in which:

FIG. 5 is a detailed diagram of a moveable belt collection system in accordance with an example embodiment.

FIG. 6 is a detailed diagram of a portion of a collection system including a centrifugally contained fluid film in accordance with an example embodiment.

FIG. 7 is a detailed diagram of a collection and segregation system in accordance with an example embodiment.

FIG. 14B is a section view taken along A-A of FIG. 14A.

FIG. 14C is a detail view of circle B in FIG. 14B.

FIG. 15 is a flow diagram for a method of extracting botanical oils from botanical materials without the use of a solvent, in accordance with an example embodiment.

Similar reference numerals may have been used in different figures to denote similar components.

DETAILED DESCRIPTION OF EXAMPLE EMBODIMENTS

Figure 1:
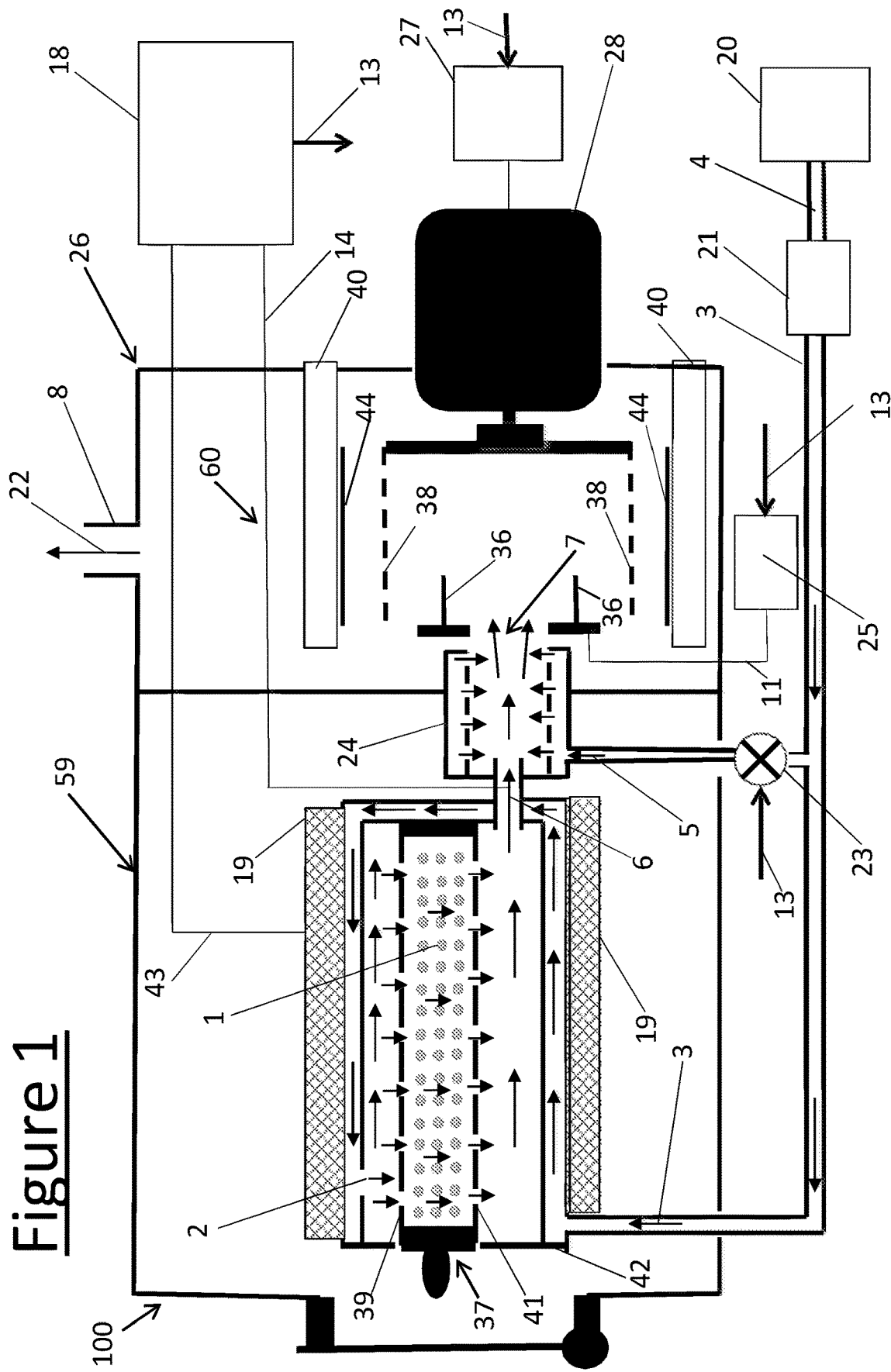
FIG. 1 is a schematic diagram of an example embodiment of a botanical extraction system.

Example embodiments include a system and method for extracting and separating botanical oils and compounds from botanical material comprising a vaporizing section which is further coupled to a centrifugal electrostatic precipitator for collection and segregation. The vaporizing section receives the botanical material through which a temperature-controlled inert gas is passed to evaporate specific vaporization temperature oils or compounds from the botanical material. The extracted vapor passes to the precipitator where the oil or compound is reduced back to the liquid state and is collected and segregated. The oils having the lowest vaporization temperature are collected first and the remaining oils are collected afterwards by specific and progressive vapor temperature control. Selected vaporized compounds are exhausted as vapor by bypassing the precipitator at specific known vaporization temperatures, thereby eliminating potentially toxic or undesirable oils or compounds from being collected.

According to an example embodiment, there is provided a system for extracting compounds from botanical material, comprising: a heater for sequentially vaporizing the botanical material at specified temperature values, each specified temperature value causing a respective vaporization temperature of one or more of the compounds in the botanical material to result in respective vaporized one or more compounds; a gas inlet for receiving an inert gas, the inert gas being for sequentially aerosolizing each of the respective vaporized one or more compounds into respective aerosolized one or more compounds; a corona electrode for sequentially charging each of the respective aerosolized one or more compounds; an electrostatic precipitator including a frame having a metal screen and the metal screen defines an interior for receiving and sequentially precipitating each of the respective charged aerosolized one or more compounds into respective precipitated one or more compounds, a motor for controlling rotation the frame having the metal screen around an axis of rotation to perform said precipitating; and a collection system at least part of which is positioned radially exterior from the frame having the metal screen with respect to the axis of rotation, the collection system for sequentially collecting each of the respective precipitated one or more compounds for each specified temperature value that are externally centrifugally expelled from the frame having the metal screen when the frame is rotated.

An example embodiment is method for extracting compounds from botanical material, comprising: sequentially vaporizing, using a heater, the botanical material at specified temperature values, each specified temperature value causing a respective vaporization temperature of one or more of the compounds in the botanical material to result in respective vaporized one or more compounds; for each of the vaporized one or more compounds from each specified temperature value: aerosolizing, using an inert gas, the respective vaporized one or more compounds into respective aerosolized one or more compounds, charging, using a corona electrode, the respective aerosolized one or more compounds, precipitating, within an interior of a metal screen of a frame, the respective charged aerosolized one or more compounds into respective precipitated one or more compounds, by rotating the frame using a motor, and collecting the respective precipitated one or more compounds that are externally centrifugally expelled from the frame having the metal screen when the frame is rotated.

According to an example embodiment, there is provided a system and method for extracting and separating various botanical oils and other compounds from botanical materials without the use of solvent chemicals, using a device having a first section configured to receive milled botanical material, and a second section in fluid communication with said first section. The method comprises of the steps of: heating the oil and other compound containing material in the first section by way of flowing heated inert gas over the oil containing botanical material in a similarly heated inert enclosure to a first temperature value sufficient to vaporize a specific botanical oil or compound characterized by a specific vaporization temperature, which flows into the second section and; converting in the second section the vaporized botanical oil or compound into an aerosol by mixing it with additional cooler inert gas to convert the vapor back into suspended liquid droplet aerosol, which is then precipitated in a centrifugal electrostatic precipitator and centrifugally expelled from the electrostatic precipitator onto a part of a collection system.

The method may further comprise using the measured first section vapor/gas exit temperature to identify specific vaporized oils or other compounds, and as a control parameter for the activation or deactivation of the aerosolization and centrifugal electrostatic precipitation process step, at specific measured first section exit temperatures or over a specific controlled first section exit temperature. Activation of the aerosolization and precipitation process step at specific measured exit temperatures or over specific controlled first section exit temperatures, allows for the subsequent collection of oils or compounds having specific vaporization temperatures.

Deactivation of the aerosolization and precipitation process step at specific first section measured exit temperatures, over specific controlled first section exit temperatures and/or bypassing the vapor around the second section allows for the subsequent exhausting of specific vapor temperature vapors from a vapor exhaust exit either directly or from the second section exhaust exit, thereby separating one or more specific unwanted vapor temperature oils or compounds from other desired specific vapor temperature oils or compounds and or preventing any contamination of the second section by undesired vapors.

According to an example embodiment, the liquid oils or other desired compounds may all be deposited onto a single removable collection surface by the centrifugal expulsion from the centrifugal electrostatic precipitator.

According to another example embodiment, the desired liquid oils may be deposited onto a single movable surface, which is in motion or is displaced periodically, such to cause the deposition of different vaporization temperature compounds onto different positions of the moveable surface, and as such result in categorization or fractionation of the oils or compounds as a function of position on the moveable surface. The moveable surface may be in the form a continuous belt of any suitable form, arranged to be surrounding the centrifugal electrostatic precipitator.

According to another example embodiment, there is provided the system including the first section vaporizer and the second section aerosolizer, centrifugal electrostatic precipitator and alternately comprising a centrifugally contained flowing film of distilled water or other suitable fluid, around the outside of the centrifugal electrostatic precipitator instead of the movable surface belt system, arranged to capture and transport the precipitated oil or other compound spun off from the centrifugal electrostatic precipitator and routed to a single fluid exit conduit for external collection in a single fluid vessel. The collected distilled water or other suitable fluid under the oil may subsequently be evaporated or drained from the collection vessel as required. Alternately the oil or other compound may be removed from the collection vessel to separate it from the distilled water or other suitable fluid.

According to another embodiment, the system including the centrifugally suspended flowing distilled water or other suitable fluid film around the outside of the centrifugal electrostatic precipitator, arranged to capture and transport the precipitated oil or other compounds spun off from the centrifugal electrostatic precipitator and routed to a single fluid exit conduit for external collection, also comprises a third collection section. The collection section is comprised of a series of removable liquid collection vessels which may be automatically positioned at a single common second section liquid output conduit, by use of a controlled carousel or other mechanical arrangement configured to position separate fluid collection vessels at specific first section exit vapor temperature values, such to collect specific vapor temperature compounds into specific collection vessels, thereby separating and distributing the various vapor temperature oils or other compounds into separate specific collection vessels. The remaining distilled water or other suitable fluid below the oil in the vessels may subsequently be evaporated or drained from the vessels to leave only the specific oil or other compound. Alternately, the oil or other compound may be removed from the vessels separating it from the distilled water or other suitable fluid.

Reference will be made below in detail to exemplary embodiments which are illustrated in the accompanying drawings. Wherever possible, the same reference numerals used throughout the drawings refer to the same or like parts.

FIGS. 1 to 4 and 11 illustrate example embodiments of a system 100 for extracting liquid oil droplets 12 from oil containing botanical material 1 without the use of liquid solvents or solvent chemicals. An example botanical material 1 is cannabis botanical material. The botanical material 1 can include a multiplicity of oils and other compounds. For example, a few of the many compounds cannabis botanical materials include at least some of the following which have different vaporization temperatures, at 0.05 mmHg (0.006666119 kPA): Cannabigerol (CBG, 52 Degrees C.), Toluene (110.6 Degrees C.), Beta-Caryophyllene (119 Degrees C.), Beta-Siteosterol (134 Degrees C.), Delta-9-Tetrahydrocannabinol (THC, 157 Degrees C.), Cannabidiol (CBD, 160-180 Degrees C.). There are many other known compounds some of which are desirable compounds and others, which are classified as toxins, have well defined vaporization temperatures greater than 180 Degrees C. and extending to above 230 Degrees C. In addition to compounds, in some examples, separation can be performed to extract specified compositions and specified elements, as applicable. Any of the described vaporizing temperatures presume 0.05 mmHg unless otherwise noted, and can be adjusted for changes in pressure, as applicable. For example, adjustment may be applied either by monitoring the pressure and compensating the temperatures or by controlling the operating pressure.

In some examples, pressure can be increased by introducing an inert gas such as Argon gas, thereby increasing the required respective vaporizing temperatures. In some examples, pressure can be reduced which reduces the vaporization temperature of the compounds in the botanical material 1, for example using a vacuum, controllable valve, pressure relief valve, pressure chamber, or a combination thereof. In some examples, the environmental operating pressure may be adjusted by the process controller 18 when it is desired to alter the vaporization temperatures. For example, reducing the pressure lowers the required respective vaporization temperature, which is useful for compounds that may be damaged at higher temperatures, e.g. in some other pharmaceutical, chemical, cellular, or organic applications.

Referring to FIG. 1, in general terms the system 100 is configured to receive botanical material 1 containing a number of compounds having different vaporization temperatures. The material is heated by flowing heated regulated Argon gas 3 from the gas inlet 2 over the botanical material in a similarly heated enclosure having an environment of inert heated regulated Argon gas 3 from the gas inlet 2 to specific temperature values for specific time durations, the process starting at the lowest vaporization temperatures such to vaporize the most volatile compounds first having lower vaporization temperatures (e.g. lower than 52 Degrees C.), followed by subsequently higher temperatures in order to vaporize the higher vaporization temperature compounds last in order to individually vaporize specific compounds. A centrifugal electrostatic precipitator 60 is used to individually precipitate each respective specific compound that are vaporized at each specific temperature value, for collection.

Due to the inert Argon gas 3 from the gas inlet 2, the heating to specific temperature values for specific time durations is performed without oxidation, as no oxygen or gas contaminants are present in the environment of Argon gas 3. As well, solvents (solvent chemicals, liquid solvents or otherwise) are not required for the heating during the vaporization and precipitation of any of the compounds of the botanical material 1.

Figure 8:
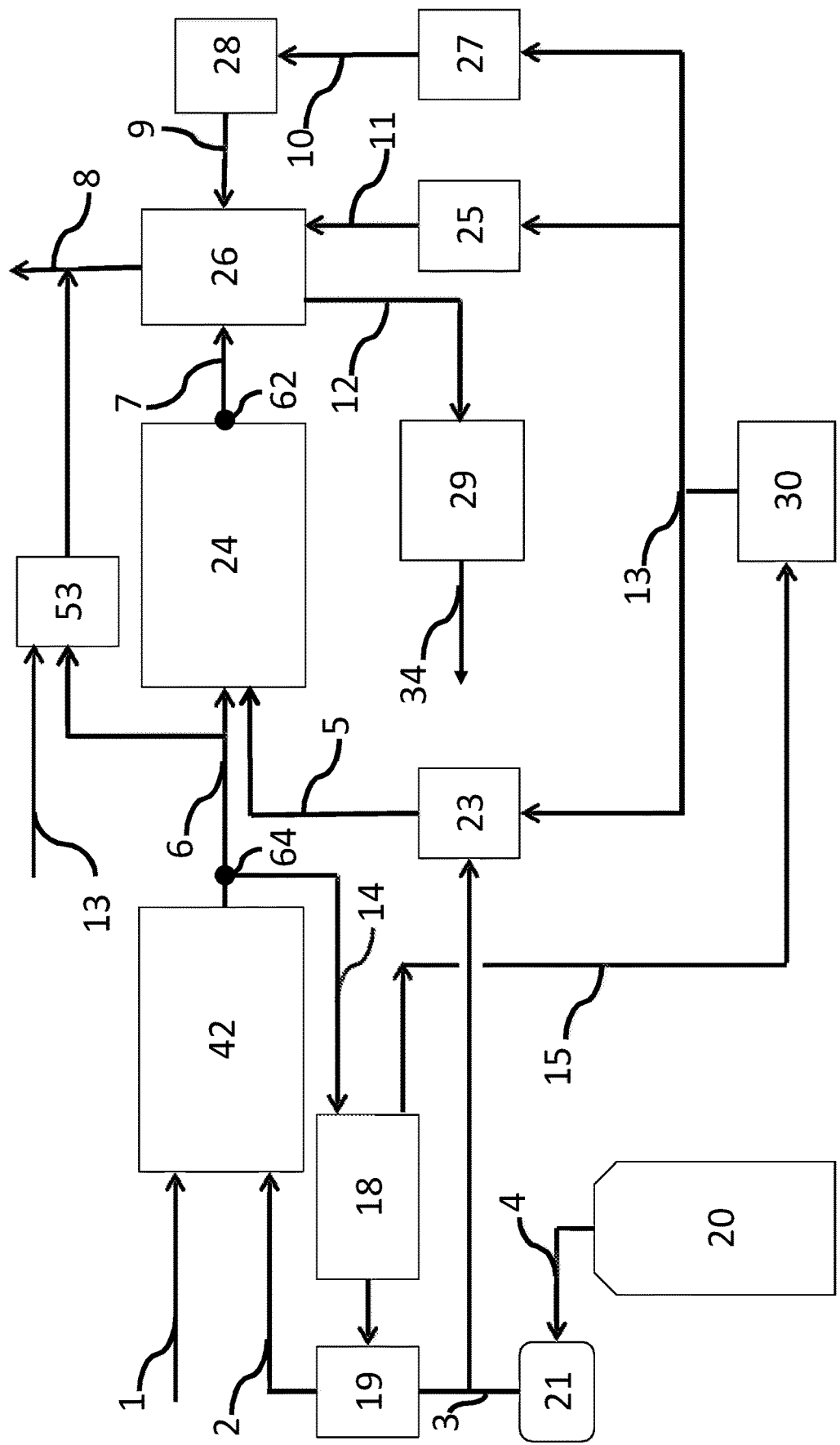
FIG. 8 is a process flow diagram for a method of extracting botanical oils from botanical materials without the use of a solvent, using the system of FIG. 1.
Figure 9:
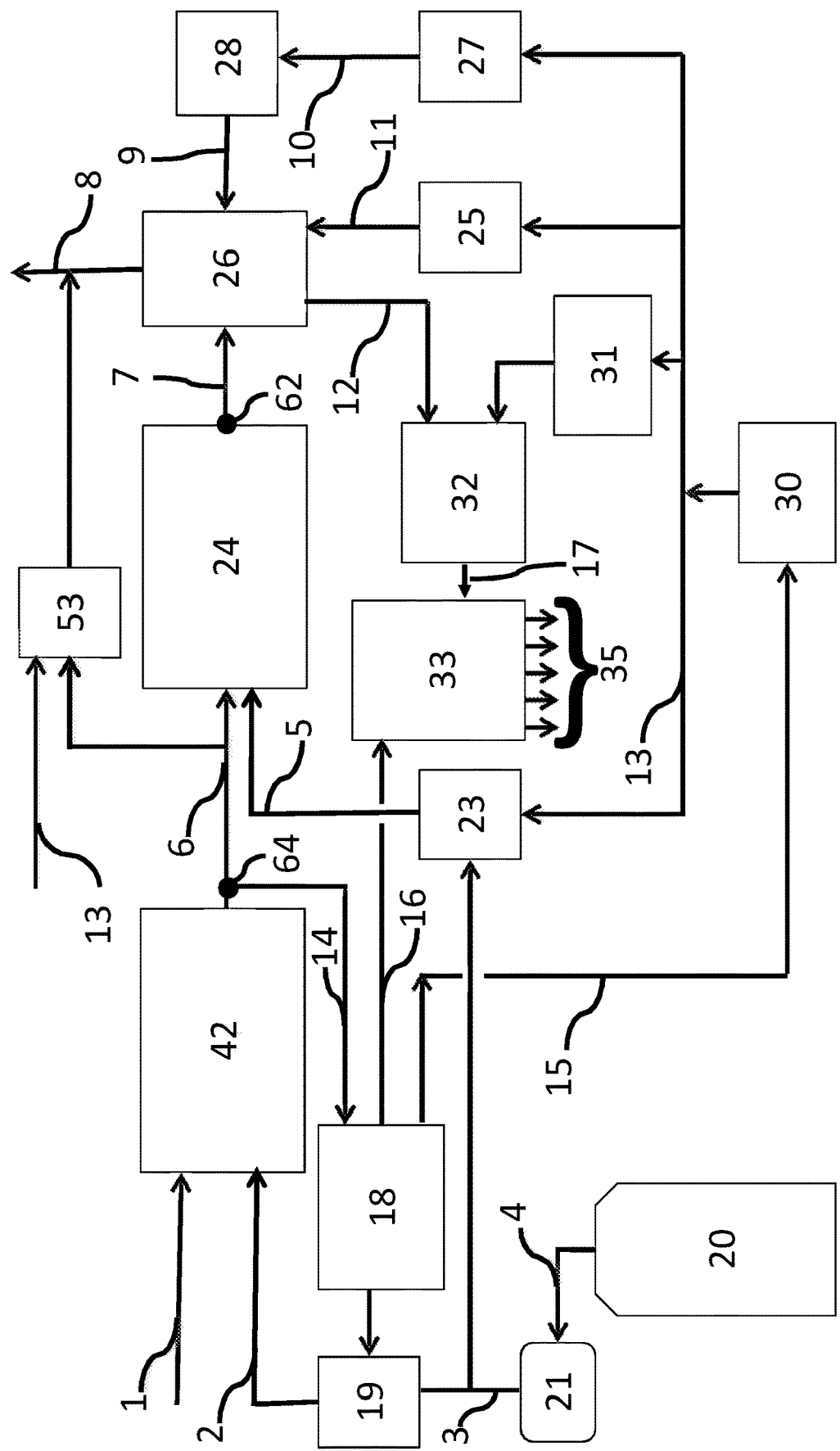
FIG. 9 is a process flow diagram for a method of extracting botanical oils from botanical materials and segregating and distributing the oils into specific collection vessels based on vaporization temperature and exhausting selected vapors based on vapor temperature for separate processing or disposal, using the system of FIG. 3 or FIG. 6.

The system 100 can be controlled by one or more controllers, for example process controller 18 and controller 30 (see FIG. 8 and FIG. 9). The process controller 18 is used to detect and control the overall components and functions of the system 100. The process controller 18 can output a respective control signal 13 to control the various components. The process controller 18 can receive signals from various sensors and detectors of the system 100. Another controller 30 (see FIG. 8 and FIG. 9) can receive a control signal 15 from the process controller 17 and can output one or more control signals 13 to enable and disable electrostatic precipitation and aerosolization. In some examples, each of the controllers 18, 30 can include a processor that executes instructions stored in a non-transitory computer readable medium. The controllers 18, 30 can be combined in a single controller in some examples, or can each have their functions performed by a plurality of controllers in some examples. In some examples, the controllers can be hardware, software, or a combination of hardware and software.

An inert gas such as Argon gas is used in example embodiments. Argon gas is provided by Argon supply 20 as high pressure Argon gas 4 and then pressure regulated through Argon pressure regulator 21, to output regulated Argon gas 3.

The inert gas such as Argon gas is used to reduce the potential of oxidation processes during the vaporization stage and to prevent combustion of potentially combustible materials that may be a part of the botanical oil containing materials. The use of an inert gas in conjunction with an electrostatic precipitation stage also minimizes the potential of Ozone ($O_3$) production as well as Nitrous Oxide ($N_2O$) production eliminating other chemical reactions that may occur due to ionization effects that can happen with air in electrostatic precipitators.

The system 100 can include a housing that defines one or more sections, including a vaporization section 59 and a precipitator section 26. The specified temperature values can be pre-programmed in a sequence into the process controller 18, based on a time sequence in some examples, or based on sensor detection to proceed to the next compound in the sequence in some other examples. The vapor produced in the vaporization section 59 (having a semi-sealed oven enclosure 42) is continuously passed on to the mixer section 24, wherein at specific predefined temperature values, unheated Argon gas 5 is introduced using an associated gas inlet and mixed with the hotter vapor, in order to reduce its temperature to cause the vapor to revert to an aerosol state of suspended condensed droplets of the previously vaporized compound. The output from the mixer section 24 is aerosolized oil or other compound and Argon 7.

A precipitator section 26 houses the centrifugal electrostatic precipitator 60. At the same instant the unheated Argon gas 5 is activated using the solenoid valve 13 to flow throw the associated gas inlet, the centrifugal electrostatic precipitator 60 is also activated in order to start the precipitation process, which coalesces the aerosolized compound onto a rotatable precipitator electrode 38 that is rotating using a motor 28 having a rotor, and the rotatable precipitator electrode 38 includes a generally cylindrical frame made of a coarse metal screen. The coarse metal screen can be a stainless steel mesh, or other metal mesh. The coarse metal screen supports a very fine metal screen on its inside diameter, which forms the electrostatic precipitator ground electrode which facilitates the centrifugally generated flow of the electrostatically precipitated/coalesced liquid on the inner surface of the fine metal screen through both rotating metal screens. In an example, the size of apertures of the fine metal screen are of a size that permits passage of the oil droplet size of the coalesced liquid. In an example, the rotatable precipitator electrode 38 (e.g., the fine metal screen and the coarse metal screen) is grounded to ground or Earth ground, or controlled to be zero volts by an electrostatic power supply 11 or a suitable switch, for attracting of charged particles. In other examples, the rotatable precipitator electrode 38 is controlled by the electrostatic power supply 11 to be a controlled voltage that is different than the charge of the charged particles. The coalesced liquid is centrifugally ejected from the rotatable precipitator electrode 38 (when rotating) and collected by example collection systems 29 as further described herein. In an example, the used Argon gas 22 is exhausted out of the precipitator section 26 via a gas path exhaust conduit 8, which also carries un-precipitated vapor present when the aerosolization-precipitation process is not activated, resulting in the exhausting and expelling of undesired vaporized compounds. The exhaust may be further processed in a separate system (not shown) as required. The rotatable precipitator electrode 38 is rotated at a fixed high speed by the motor 28, such as 4000 revolutions per minute. In some examples, the rotatable precipitator electrode 38 is controlled to be rotated at variable speeds (e.g. partial speed, periodic modulating speed or sinsusoidal modulating speed) rather than a fixed maximal speed. In other examples, other actuators or drivers can be used instead of the motor 28.

In one example embodiment, the vaporization section 59 is configured to receive botanical material 1 that is milled and contained in a drawer type cartridge 37. The botanical material 1 includes a multiplicity of compounds having different vaporizing temperatures. The drawer type cartridge 37 containing the botanical material 1 is then inserted into the semi-sealed oven enclosure 42, which is in the vaporization section 59 that is generally used to receive the botanical material 1 and for controlled vaporization of the botanical material 1. In some examples, the drawer type cartridge 37 is removable, and after processing and extraction, the drawer type cartridge 37 is removed and the next drawer type cartridge 37 containing the next botanical material 1 is inserted into the semi-sealed oven enclosure 42. See, for example, FIG. 10 which illustrates the next drawer type cartridge 37 that can be processed and collected.

At the beginning of the process following the installation of the botanical loaded drawer type cartridge 37, the semi-sealed oven enclosure 42 is initially flooded with a pre-set flow of ambient temperature Argon gas 3 from the gas inlet 2 to substantially remove any oxygen from the enclosure environment of the vaporization section 59 and the precipitator section 26, and also to some degree from the enclosure of the loaded drawer type cartridge 37 and the botanical material 1 contained within. In some examples, at the same time as the initial flooding with the Argon gas 3 from the gas inlet 2, a vacuum suction is used to partially or fully evacuate the semi-sealed oven enclosure 42, the mixer section 24, and the precipitator section 26, to initially remove oxygen and other ambient gases via the gas path exhaust conduit 8.

The drawer type cartridge 37 and the semi-sealed oven enclosure 42 are arranged such that Argon gas 3 from the gas inlet 2 is forced to flow through the containment screen 39 on the upper surface (top sidewall) of the drawer type cartridge 37 through the milled botanical material 1 and out through the containment screen 41 on the lower side (bottom sidewall) of the drawer type cartridge 37. Some examples include recirculated Argon gas 22 from the gas path exhaust conduit 8 in addition to or in place of Argon gas 3 from the Argon gas supply 20. In some examples, an initial injection of Argon gas 3 is provided by the Argon gas supply 20, followed by recirculation of any of the used Argon gas 3 to the extent possible.

The flowing Argon gas 3 and the semi-sealed oven enclosure 42 are gradually heated at a controlled rate by a heat source 19 (heater) to a first specified vapor temperature value that corresponds to a desirable compound vaporizing temperature of one or more of the compounds within the milled botanical material 1. In an example, the heat source 19 can generally surround the semi-sealed oven enclosure 42 and the gas inlet 2. The temperature 14 of the oven exit vapor 6 of the semi-sealed oven enclosure 42 is detected by one or more respective temperature sensors 64, and the temperature 14 is received, monitored and controlled by the process controller 18, by using the heat source 19 to controllably heat both the Argon gas inlet 2 and a wall temperature of the semi-sealed oven enclosure 42, simultaneously. In some examples, the heat source 19 can have the desired specified temperature regulated using feedback from the temperature 14 of the exit vapor 6 (by one or more temperature sensors 64). In some other examples, the heat source 19 is self-regulated and/or calibrated to provide the desired temperature 14 of the exit vapor 6.

In some examples, the temperature that the Argon gas 3 is heated through the gas inlet 2 into the semi-sealed oven enclosure 42 before it encounters the milled botanical material 1 is higher than (greater than) the specific vapor temperature being targeted. The higher temperature by the heat source 19 is used prior to entry to the semi-sealed oven enclosure 42 because, in an example, the measured temperature of the exit vapor 6 from the semi-sealed oven enclosure 42 is used for the control feedback for the controlling of the heat by the heat source 19 being input to the semi-sealed oven enclosure 42. The actual temperature of the Argon gas 3 will cool by some amount as the particular compounds of the milled botanical material 1 are absorbing energy when being vaporized (heat of vaporization is supplied by the energy in the Argon gas to the milled botanical material 1). In some examples, one or more temperature sensors 64 detects the temperature of the exit vapor 6 immediately as the vapor is formed, and the temperature is used as a control or process value that is measured and fed back to the heater power control input though the process controller 18. The power to the heat source 19 is controlled by the process controller 18 to maintain the vapor on vaporization to a specific temperature, not to control the temperature of the gas being supplied to the vaporizer (this is how the energy reaches the material), which is used to vaporize the compound. The vapor temperature upon evaporation of the exit vapor 6 will be at the vaporization temperature of the compound (this is measured right at the exit of the drawer type cartridge 37 since it could become heated or cooled further downstream of this location). If the gas flow rate varies, the input gas temperature will vary by control from the process controller 18 to compensate and hold the vapor temperature fixed at the controlled value by the feedback loop controlling the power to the heat source 19.

Since the compound vapor temperatures are defined by the chemistry of the compound (at any given pressure), the vaporization temperature identifies the specific compound. By controlling the vapor temperature at vaporization by adjusting the power (heat input) supplied by the heat source 19 to the (un-defined) gas flow, the process controller 18 automatically controls the actual heat of vaporization, input to the (un-defined amount of) compound from the milled botanical material 1 for any specific compound having a given vaporization temperature.

In some examples, the process controller 18 detects the completion of vaporization at any given control temperature (compound or group of compounds) by the impedance characteristic (e.g., using an electrical energy sensor 62 such as a voltage sensor and/or current sensor) within the centrifugal electrostatic precipitator 60, thus determining when a specific vapor is partially or completely evaporated and collected (or removed). The particular variable impedance characteristic can be detected by one or more sensors, or calculated from sensor information from those one or more sensors. The detection of a breakdown voltage of a spark gap can be used in some examples in place of the impendence sensor to determine that a specific vapor is completely evaporated and collected (or removed), or is below a threshold. The sensor information to determine the impedance characteristic can be used by the process controller 18 for vaporizing of the next one or more compounds from the milled botanical material 1 having the next higher respective vaporizing temperature.

After flowing the Argon gas 3 via gas inlet 2 through the botanical material 1, the vaporized compounds mixed with Argon as exit vapor 6 flows into a mixer section 24, wherein at the first specified temperature value the vapor is mixed with a separate controlled flow of unheated Argon gas 5 as the process controller 18 activates flow of the unheated Argon gas 5 via a solenoid valve 23 at said first specified temperature value.

Figure 4:
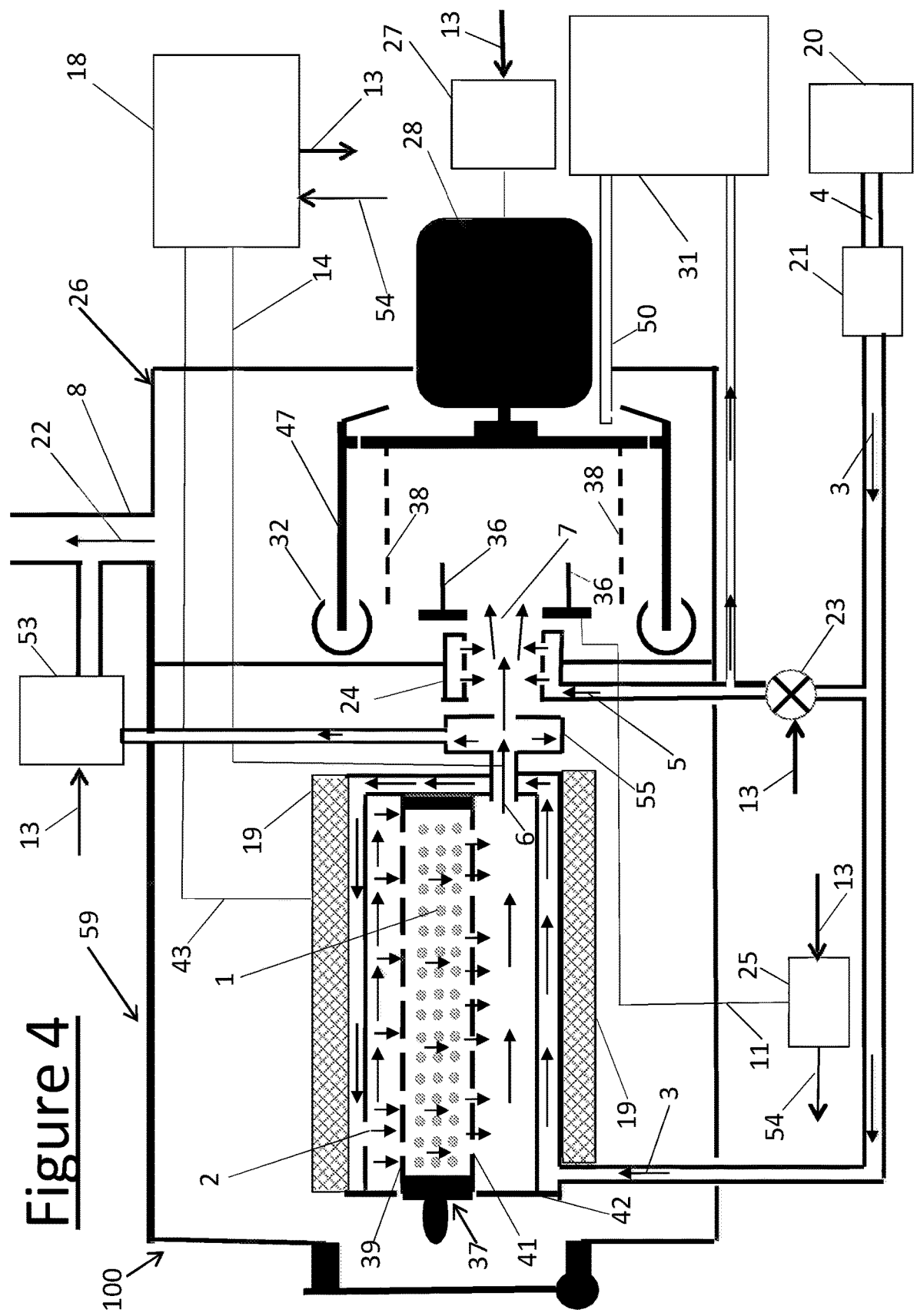
FIG. 4 is a schematic diagram of a fourth example embodiment of a botanical extraction system including a vapor bypass system to reduce potential contamination of a centrifugal electrostatic precipitator of the botanical extraction system when deactivated.

FIG. 4 is a schematic diagram of a fourth example embodiment of a botanical extraction system including a vapor bypass system to reduce potential contamination of the centrifugal electrostatic precipitator 60 when deactivated. Until the first specified temperature value is reached, any vapors that may be exiting from the vaporizer section is not mixed with cooler Argon gas 5 and flows through the precipitator section 26 and out of the gas path exhaust conduit 8 and or flows directly out of the bypass annulus 55 (or other exhaust outlet or exhaust cavity) and out of the gas path exhaust conduit 8. In addition to no flow of unheated Argon gas 5 prior to the first specified temperature value, the electrostatic power supply 11 to one or more corona electrodes 36 is held at zero voltage by power supply 25, to prevent charging of the vapors and any corona action from the corona electrodes 36, and thereby disabling electrostatic precipitation from occurring in the rotatable precipitator electrode 38.

Referring still to FIG. 4, the motor 28 used to drive the rotatable precipitator electrode 38 is also controlled to operate at zero or a low speed prior to the any specified temperature value being attained to prevent potential impact related coalescence of the undesired vapors, as they pass through the inoperative centrifugal electrostatic precipitator 60 and out of the gas path exhaust conduit 8, and/or the vapors are bypassed around the precipitator section 26 via the annular bypass duct 53 thus exhausting unselected compounds from the system 100 prior to the specified temperature value being attained by the temperature 14 of the exit vapor 6. Further treatment or processing may be applied to the exhaust vapors from the gas path exhaust conduit 8 in a separate system (not shown) as required. In some examples, the Argon gas 22 exhausted from the activated centrifugal electrostatic precipitator 60 is recirculated (having been electrostatically cleaned by the centrifugal electrostatic precipitator 60) through one circuit to the heater and drawer type cartridge 37 and also via a cooling heat sink (e.g., heat sink tube 80, FIG. 13) to the mixer section 24 for re-injection into the precipitator 60. In such examples the un-heated Argon supply 20 from the Argon pressure regulator 21 may be reduced or stopped to conserve Argon gas consumption. In such an arrangement, the Argon gas supply 20 may only be used when un-precipitated vapors are exhausted from the system 100 to replace any Argon gas lost in the exhaust, or when additional Argon gas is required (e.g. to increase the present pressure).

Once the first specified temperature value has been attained, compounds of that specific vaporization temperature will begin to vaporize rapidly from the botanical material 1 and will be transported as hot exit vapor 6 from the semi-sealed oven enclosure 42 into the mixer section 24 where the bypass to bypass duct 53 has been deactivated and the unheated regulated Argon gas 5 is activated as the first specified temperature value is reached, and the charge of the centrifugal electrostatic precipitator 60 is activated and rotation action using the motor 28 is activated to rotate the centrifugal electrostatic precipitator 60 around an axis of rotation. The vaporization temperature of each respective compound is at least the boiling point of that compound, taking into account the present pressure (the present pressure can be controlled in some examples).

The hot exit vapor 6 can be mixed with unheated Argon gas 5 and as a result will suddenly cool to a temperature below the vaporization temperature, causing the vaporized compound to begin to condense into an aerosol of suspended microscopic droplets, which becomes exposed to the now activated generated ions from the corona electrodes 36, resulting in electrostatic charging of the suspended droplets, and the subsequent electrostatic attraction to the (now rotating) rotatable precipitator electrode 38. The rotatable precipitator electrode 38 is conductive due to the fine stainless steel screen. In some examples, the precipitator electrode 38 is grounded, forming a grounded plate electrode of the centrifugal electrostatic precipitator 60.

The electrostatic action results in the microscopic droplets and possibly remaining vapors to coalesce as a liquid into the rotating rotatable precipitator electrode 38. As the droplets collect on the fine stainless steel screen and coalesce into larger liquid droplets, the centrifugal forces that build up as the droplet mass increases with size, causes the larger droplets to be ejected free from the rotating rotatable precipitator electrode 38 outside surface in a tangential direction, to be captured by one of several different possible collecting systems to be described in more detail below. The remaining Argon gas and any potentially un-precipitated vapor pass out of the precipitator section 26 via the gas path exhaust conduit 8 or in some examples are re-circulated for re-use (the recirculation is explained in greater detail herein).

After a predetermined period of time or specified precipitator impedance characteristic or discharge detected signal 54 at the specific temperature value, the process controller 18 disables the aerosolization and electrostatic precipitation action by deactivating flow of the unheated Argon gas 5 and the corona electrodes 36, reactivating the bypass flow, deactivating the electrostatic power supply 11 (when used) and slowing or stopping the motor 28.

The process controller 18 then begins to increase the temperature of the semi-sealed oven enclosure 42 and Argon gas 3 through gas inlet 2 flow to achieve the next specified vaporization temperature, in a controlled ramping upwards of the temperature 14 of the exit vapor 6 of the semi-sealed oven enclosure 42 in precisely the same way as was done for the first specified temperature, whereby this identical process is repeated for any number of respective predetermined specific temperature values where the vapor temperature of desired compounds are known.

In some cases there are compounds which are not desired to be collected and have known vapor temperatures, for example at 0.05 mmHg: Toluene at 110.6 Degrees C., or Benzene at 200 Degrees C. or Naphthalene at 218 Degrees C., which are all listed as toxic compounds. Some of these particular compounds can have vapor temperatures below some desirable compounds (e.g. lower than 52 Degrees C.) and above others (e.g. greater than 180 Degrees C.), and can be evaporated and disposed of from the milled botanical material 1 by attaining the specific vaporization temperature values for a specific period of time but without activating the precipitator section 26, and/or selectively bypassing the vapors around the precipitator section 26 such to exhaust these undesirable compounds as un-precipitated vapor, preventing any specifically selected compounds of specific vaporization temperatures from being collected and potentially mixed with other more desirable compounds. The exhausted vapors may undergo further treatment or processing in a separate system in some examples (not shown).

The liquid oil droplets 12 are precipitated compounds by the centrifugal electrostatic precipitator 60 and are ejected from the centrifugal electrostatic precipitator 60, which are then collected in one of several possible different collection systems 29 which range from very basic arrangements of lower cost to more sophisticated arrangements which allow for the separate collection of each compound of a specific vapor temperature.

In an example embodiment as depicted by FIG. 1 and FIG. 8, the collection system 29 includes a removable sleeve 44, which is held in a position around the rotatable precipitator electrode 38, by a support system 40 such that the precipitated compounds (typically an oil) ejected from the rotating rotatable precipitator electrode 38 impact and attach to the removable sleeve 44 by adsorption. The removable sleeve 44 may be removed to gain access to the deposited compound and replaced with a clean removable sleeve 44 for the capture of a different vapor temperature compound, or may be left in place to collect several different compounds. The support system 40 may be cooled by some known method during operation, to allow the removable sleeve 44 and deposited compounds to be cooled as required.

Figure 2:
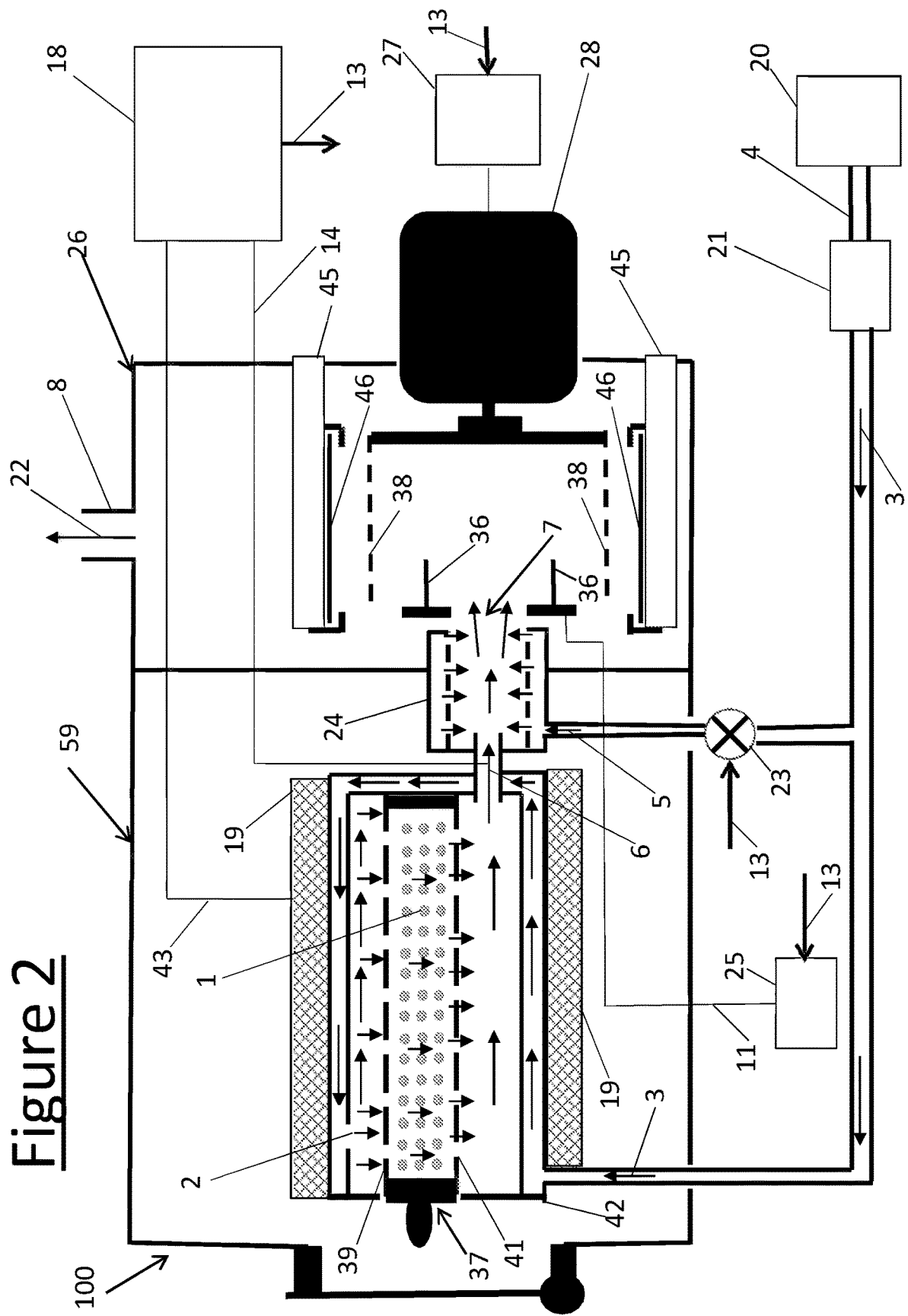
FIG. 2 is a schematic diagram of a second example embodiment of a botanical extraction system.

In another example embodiment of the system 100 as depicted by FIG. 2, FIG. 5 and FIG. 8, in this collection system 29 the removable sleeve 44 and support system 40 is replaced with a belt support sleeve 45 arranged to allow the threading of a moveable belt 46 of material, suitable for the deposition of compounds from the centrifugal electrostatic precipitator 60 (parchment paper belt or a suitable silicon compound belt of some form), such that it circumferentially surrounds the rotatable precipitator electrode 38 and provides 360 degrees of collection surface, that can be withdrawn tangentially guided by the belt support sleeve 45 so as to change the exposed 360 degree surface to a clean surface for collecting the next temperature precipitated compound, while the surface having the deposited specific compound is now exposed on the outside of the system providing access to the deposited compound. This arrangement provides a simple method to collect the compounds having different vapor temperatures while separating them from each other. The belt support sleeve 45 may be cooled by known methods to maintain the temperature of the movable belt 46 of material and deposited compound to a relatively lower temperature as required.

Figure 3:
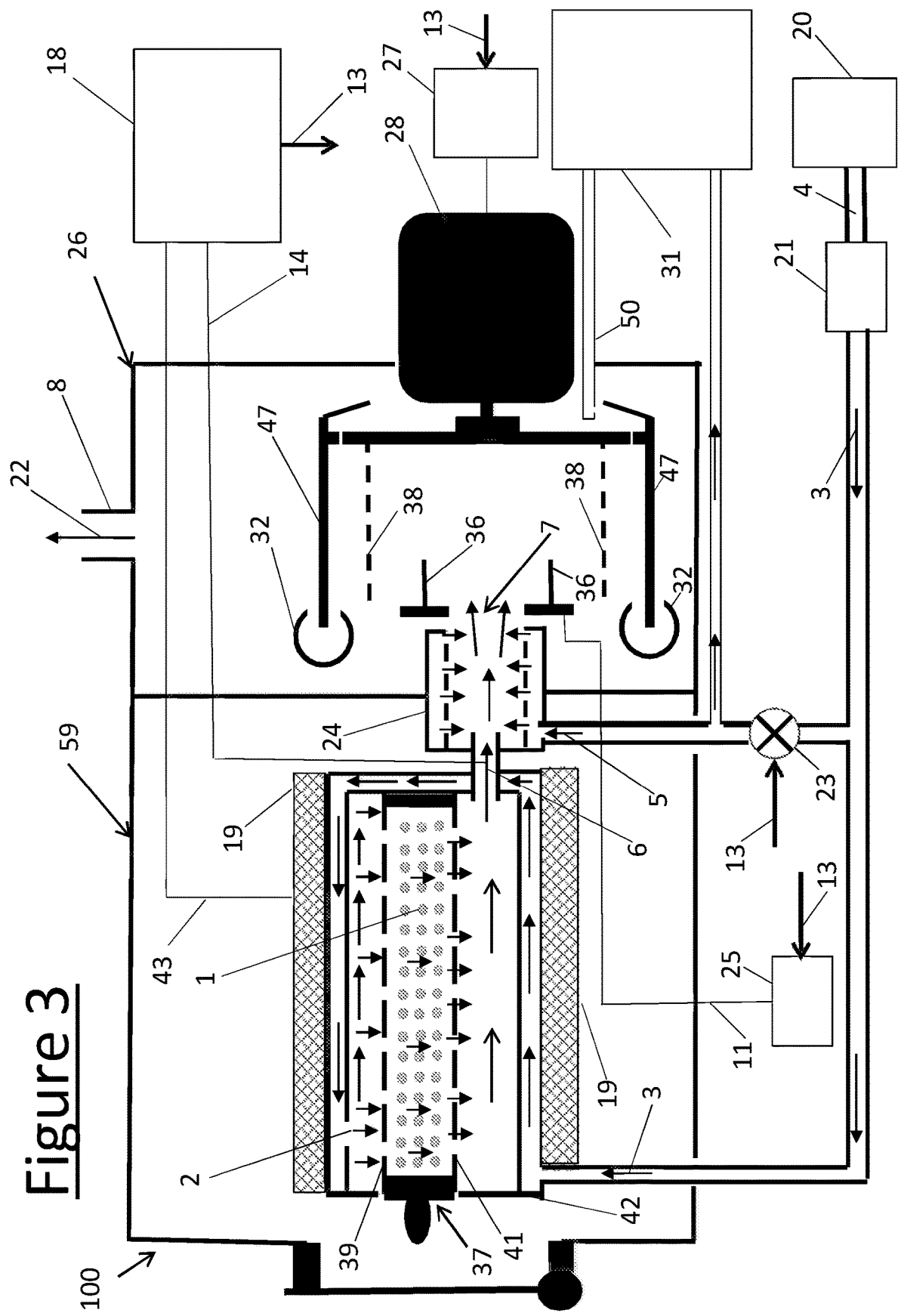
FIG. 3 is a schematic diagram of a third example embodiment of a botanical extraction system including a fluid film product collection system.

In another example embodiment of the system 100 as depicted by FIG. 3, FIG. 6 and FIG. 9, in this collection system 29 the belt support sleeve 45 and movable belt 46 has been replaced by a rotatable sleeve 47, which is attached to, and rotating with the rotor of the motor 28 that controls the rotatable precipitator electrode 38, and is further provided with a small flow of distilled water or other fluid from a controlled source of fluid supply 31 (e.g. reservoir or tank) into the motor end of the rotatable sleeve 47. The distilled water or other fluid is only fed to the rotatable sleeve 47 while the centrifugal electrostatic precipitator 60 is active, by utilizing the solenoid controlled pressure of the Argon gas 5 to pressurize the fluid supply 31, to cause distilled water or other fluid to flow through the conduit 50, when pressurized. The distilled water or other fluid introduced to the rotatable sleeve 47 is constrained by centrifugal force to form an axially flowing distilled water or other fluid film 48 along the inside surface of the rotatable sleeve 47 and flows in an axial direction towards the open end of the rotatable sleeve 47, collecting compound ejected from the rotating rotatable precipitator electrode 38, where the water or other fluid plus compound is ejected in a tangential direction from the open end of the rotatable sleeve 47 either from the edge of the rotatable sleeve 47, or from a series of radial holes (not shown) in the rotatable sleeve 47. In examples, the distilled water or other fluid is not considered a solvent here because it does not dissolve the collected compound, but rather supports motility of the collected compound. The distilled water or other fluid compound 49 is ejected from the rotatable sleeve and is captured in an annular fluid conduit 32, which is further connected to a tangentially directed drain conduit 51 (see FIG. 7).

Figure 12:
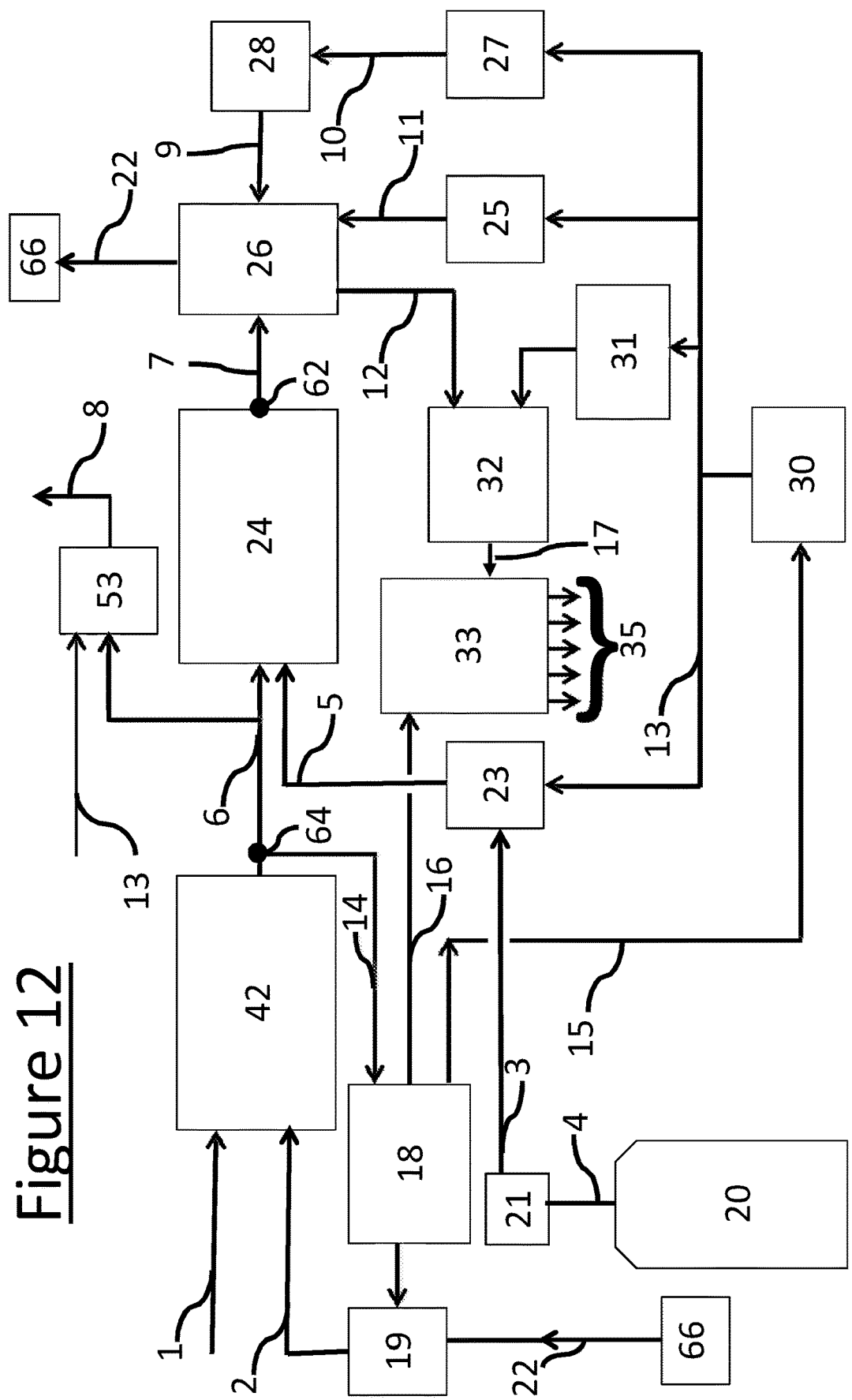
FIG. 12 is a process flow diagram for a method of extracting botanical oils from botanical materials using the system of FIG. 11.

Referring to FIGS. 11 and 14A, 14B, and 14C, in an example system 100 that includes recirculation of the Argon gas, a tangential gas duct 68 and recirculation conduit 66 located next to the annular fluid conduit 32 is arranged to carry the expelled Argon gas 22 which is being expelled from the rotatable precipitator electrode 38 from which the vapors have been precipitated from the Argon gas 22 (e.g. electrostatically cleaned) for recirculation of the Argon gas 22. FIG. 12 is a process flow diagram for extracting botanical oils from botanical materials using the system 100 of FIG. 11 and FIGS. 14A, 14B and 14C. Therefore, the system 100 can have a dual tangential duct arrangement to collect the liquid ejection separate from the Argon gas that will be ejected from the rotatable precipitator electrode 38.

In some examples, the cool Argon feed at the mixer section 24 is the only feed input for the Argon gas to the semi-sealed oven enclosure 42. In some examples, there is only recirculated Argon gas to the gas inlet 2, and no direct feed of fresh Argon gas from the Argon supply 20 to the semi-sealed oven enclosure 42 to the gas inlet 2.

The Argon gas now collected from the tangential gas duct 68 and through the recirculation conduit 66 is fed to the heat source 19, wherein the Argon gas 22 has been electrostatically cleaned in the rotatable precipitator electrode 38 and partially pressurized by the tangential ejection from the rotatable precipitator electrode 38, and the Argon gas 22 is re-circulated back to the semi-sealed oven enclosure 42 for re-use. This reduces the power requirement for raising the temperature of the Argon gas 22 and significantly reduces the potential waste of Argon gas that would otherwise be wasted in the process when the Argon gas is removed as exit exhaust only. A portion of the recirculated Argon gas flow can be cooled and used as the cool Argon gas added to the vapor flow entering the precipitator section 26 (in the mixer section 24), as an alternative to the un-heated Argon gas from the external Argon supply 20 of regulated Argon gas 3.

There are some example practical reasons for the recirculation of Argon gas 22: first, significant reduction in the consumption of Argon gas while increasing the net Argon gas flow around the circuit; second, reduced power consumption in heating the Argon gas; third, reduced temperature differential between the Argon gas (semi-sealed oven enclosure 42) and the desired vapour temperature (due to higher Argon gas through flow).

In some examples, as shown in FIGS. 14B and 14C, there are a plurality of paddle type vanes 72 attached at the exit slot on the rotatable sleeve 47. Also, there is the tangential gas duct 68 around the rotatable sleeve 47 which exits to the recirculation conduit 66, therefore the system 100 now has two separate ducts, one for the fluid (water and oil) and one for the Argon collection for recirculation which now feeds the semi-sealed oven enclosure 42 with recirculated Argon gas instead of the fresh regulated Argon gas 3 from the Argon supply 20. The fresh cool Argon gas is now supplied directly to the mixer section 24. The Argon gas 22 can also be recirculated from the rotatable precipitator electrode 38 to the recirculation conduit 66, which is pumped by the rotor tangential ejection action of the rotatable precipitator electrode 38, plus the paddle type vanes 72 in this example.

Figure 14A:
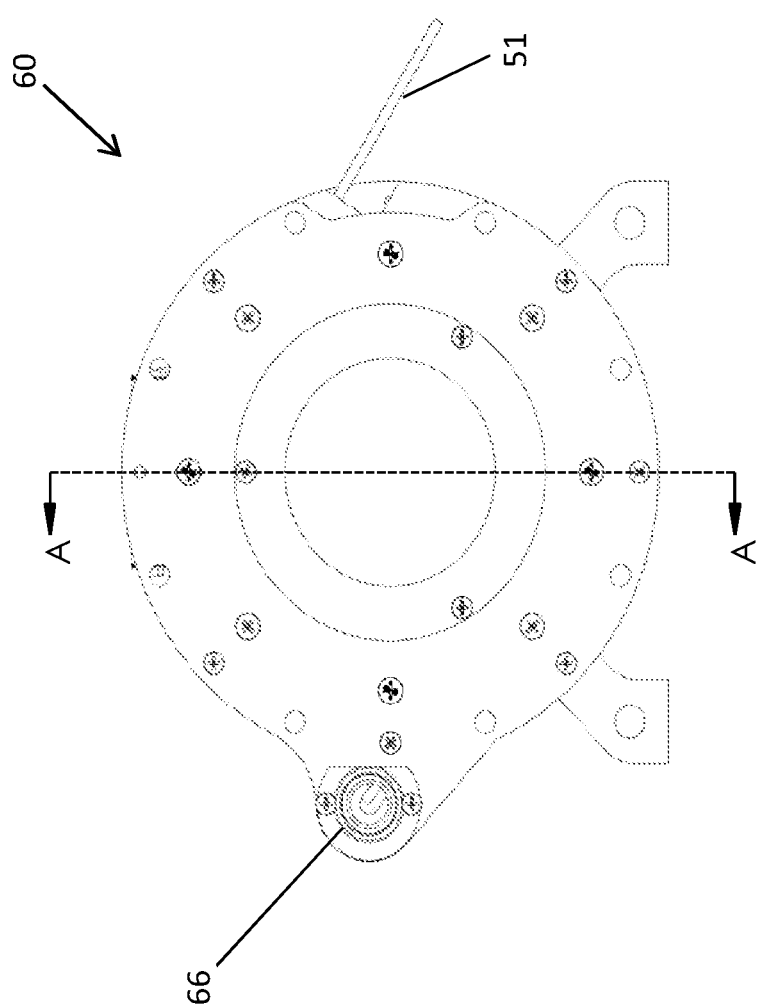
FIG. 14A is a side view of an example centrifugal electrostatic precipitator for the botanical extraction system, wherein the centrifugal electrostatic precipitator has paddle type vanes, in accordance with an example embodiment.
Figure 14F:
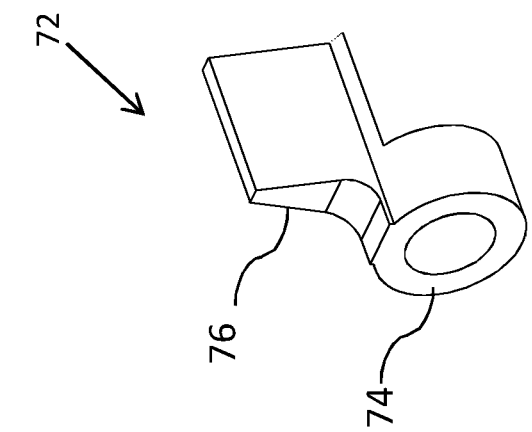
FIG. 14F is a perspective view of the paddle type vane shown in FIG. 14D.
Figure 14E:
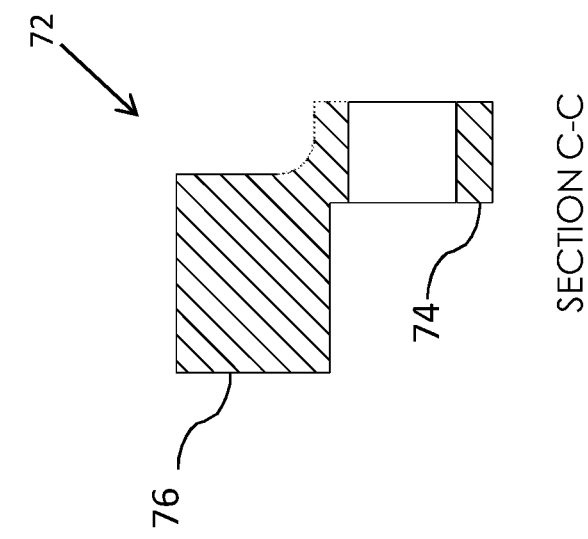
FIG. 14E is a section view taken along C-C of FIG. 14D.
Figure 14D:
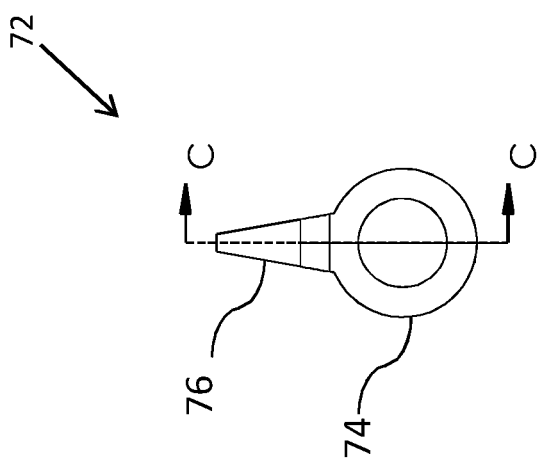
FIG. 14D is a side view of one paddle type vane for the centrifugal electrostatic precipitator shown in FIG. 14A.

FIGS. 14D, 14E and 14F illustrate one of the paddle type vanes 72 in greater detail. As shown, the paddle type vane 72 includes a mount 74 which can define an annulus. The mount 74 is fixedly mounted to the rotatable sleeve 47, and rotates along with the rotatable sleeve 47. The paddle type vane 72 includes a vane 76, wherein the vane 76 has an aerodynamic shape that rotates with the rotatable sleeve 47, to assist in flow of the recirculated Argon gas 22 to the tangential gas duct 68.

During operation of the system 100 where specific compounds are being precipitated and ejected from the rotating rotatable precipitator electrode 38, the rotatable sleeve 47 supporting the distilled water or other fluid film 48 captures the compound, which is then transported by the fluid flow 49 via the annular fluid conduit 32 and out through the drain conduit 51 (FIG. 7) where it may be collected in a collection vessel 52 of a plurality of collection vessels 52. Each collection vessel 52 can be manually or automatically changed for each specific vapor temperature compound. Since the vaporized botanical compounds are in general oils of lower density than water, the compounds will generally remain on the surface of the distilled water or other fluid and are easily separated either mechanically (not shown) or by evaporation of the distilled water or other fluid by a further system or method (not shown). FIG. 7 also illustrates the axis of rotation of the rotatable precipitator electrode 38.

In some examples (not shown), the fine stainless steel screen, the coarse metal screen, and the rotatable precipitator electrode 38 are partially conical rather than cylindrical, with the smaller radius at the end facing the distilled water or other fluid supply conduit 50 and the larger radius facing the annular fluid conduit 32. This generally conical shape facilitates flow of the water or other fluid plus compound towards the annular fluid conduit 32. The generally conical rotatable precipitator electrode 38 can be rotated along its central longitudinal axis, and generally operate in a similar manner as the cylindrical case described herein.

In example embodiments, it can be appreciated that two or more types of compounds from the botanical material 1 can be processed and collected at one time, within one iteration of the process performed by the system 100. For example, in some applications it may be desired to collectively collect both THC and CBD at one time, for example into one collection vessel 52. In such examples, the specified vaporizing temperature can be controlled via the heat source 19 to be in a range of temperatures between the vaporization temperatures of the two or more types of compounds from the botanical material 1 (THC and CBD in this example), or alternatively can be increased to and maintained at the higher vaporization temperature of the desired two or more compounds (CBD requires the higher vaporization temperature in this example).

The controller 30 is used to sense and control the various components of the system 100, including the various sensors, solenoid valve 23, the electrostatic power supply 11, the power supply 25 and the motor drive control 27, in order to enable or disable various aspects of the vaporization, electrostatic precipitation and aerosolization.

In an example embodiment of the system 100 depicted in FIG. 7 and FIG. 9, the drain conduit 51 is arranged to output the distilled water, or other fluid plus compound 49 to a collection vessel indexing system 33 for automated positioning of each collection vessel 52 of the plurality of collection vessels 52. Each collection vessel 52 is used to collect specific distilled water, or other fluid plus compound 49 (e.g. compound is suspended botanical oil), where the collection vessels 52 are each incrementally replaced for collecting at each specific vaporization temperature value. The collection vessel indexing system 33 provides for automated separation of specific botanical compounds based on each respective vaporization temperature. At least one collection vessel 52 is used to collect product 34 from the drain conduit 51. FIG. 7 and FIG. 9 illustrate multiple separated products 35, one different separated product 35 for each collection vessel 52. In other examples, more than one product 35 (but not all) is collected in at least one of the collection vessels 52. The collection vessel indexing system 33 can include a conveyor 58 such as a rotary turnstile for supporting each collection vessel 52 (see e.g. FIG. 10). The conveyor 58 can also comprise a linear conveyer belt (not shown) in other examples.

Figure 13:
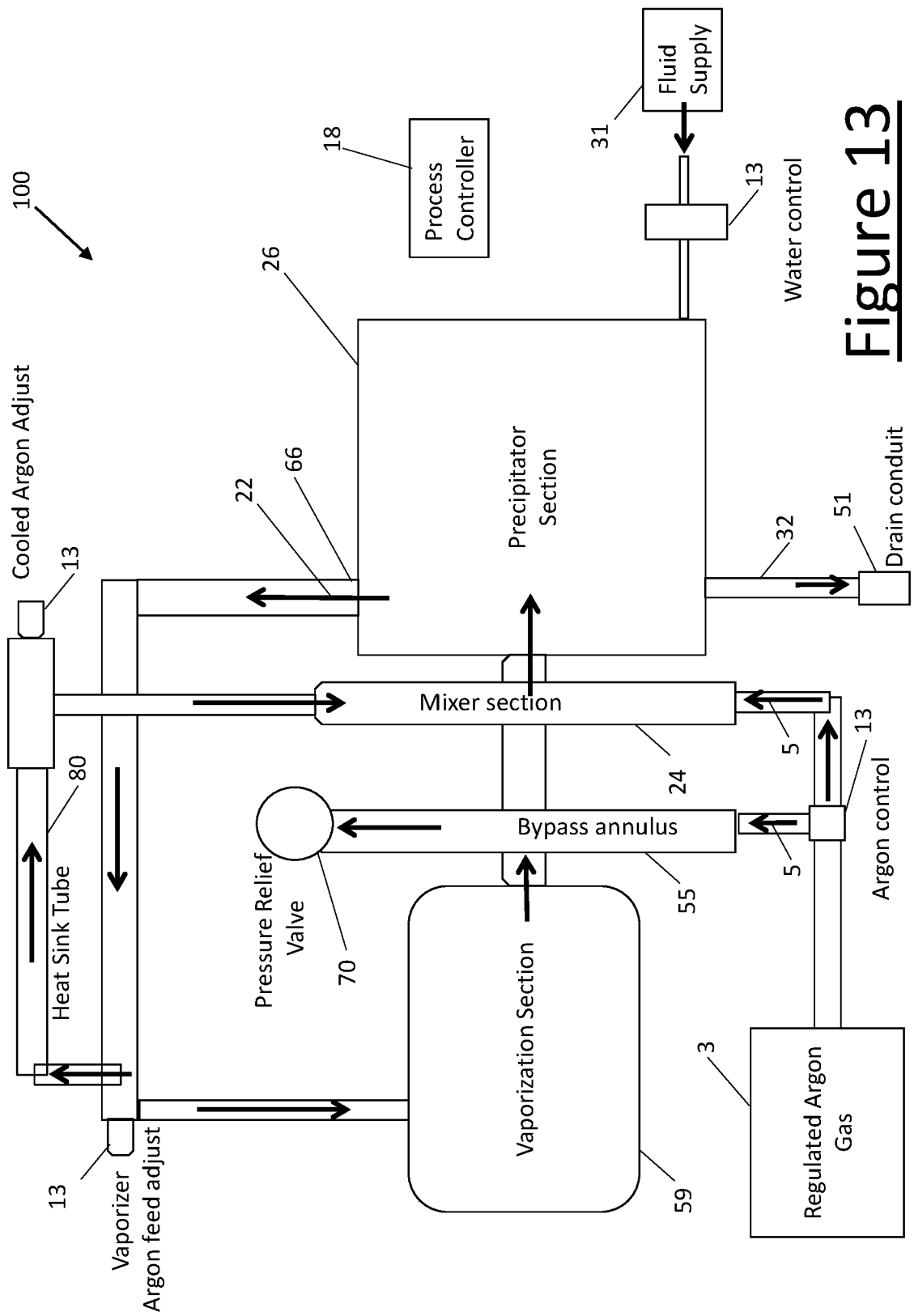
FIG. 13 is a schematic diagram of a sixth example embodiment of a botanical extraction system including a pressure relief valve for controlling an operating pressure of the botanical extraction system.

FIG. 13 is a schematic diagram of another example embodiment of a botanical extraction system 100 that includes a pressure relief valve 70 for controlling an operating pressure of the system 100. The features of the system 100 of FIG. 13 can be used in the other described examples of the system 100, e.g. as in FIGS. 1, 2, 3, 4, 11. The system 100 of FIG. 13 controls the operating pressure and also facilitates recirculation of the Argon gas flow. In some examples, the pressure relief valve 70 has a very low pressure relief valve setting, such that introducing fresh Argon gas into the bypass annulus 55 results in flow out of the pressure relief valve 70 as waste exhaust through bypass duct 53 and gas path exhaust conduit 8 (not shown here). This allows control of the maximum pressure within the complete system 100. Examples of the pressure relief valve 70 include those similar to a pressure cooker, wherein a weight on a pin arrangement or a floating metal ball is lifted by the pressure, allowing venting. The pressure relief valve 70 also helps to better define the vaporization temperatures at different location altitudes or atmospheric conditions, because the pressure relief valve 70 assists in generally maintaining the desired pressure so that the characteristic boiling points of the one or more compounds are not varying while in operation due to their dependency on pressure.

In some examples, the pressure relief valve 70 is controllably activated by the process controller 18 using a suitable control signal. A solenoid valve (not shown) can be used for the activation.

In some examples, the pressure relief valve 70 is activated by the process controller 18 by initializing input Argon flow to the bypass annulus 55, to increase pressure such to cause the pressure relief valve 70 to inherently open and as such venting from the pressure relief valve 70 the bypass circuit. The cool or un-heated Argon gas for aerosolization in the mixer section 24 will now be part of the re-circulated Argon gas after passing through a heat sink tube 80 or other cooling tube, which can be branched off, re-circulated flow, and fed back into the mixer section 24 after the cooling through the heat sink tube 80, as shown. The Argon gas input to the mixer section 24 can be used to initially charge the vaporization section 59 and the precipitator section 26 before the heating and vaporizing, allowing any air in the system to vent out via the pressure relief valve 70 while the rotatable precipitator electrode 38 is rotating. The rotating rotatable precipitator electrode 38 pumps the recirculated Argon gas flow around the system 100 so that the air in the system 100 exits via the pressure relief valve 70, and stops flowing once the process controller 18 shut off the Argon gas 5 inlet flow. To bypass un-wanted vapors, the rotatable precipitator electrode 38 is de-activated and the rotor of the motor 28 may be slowed or stopped, and the fresh Argon gas supply is turned on resulting in flow both through the precipitator section 26 and out to the vaporization section 59, and also backwards into the bypass annulus 55 and the associated exhaust cavity and out through the pressure relief valve 70 to the gas path exhaust conduit 8 (not shown here). In another example, the reduced pressure operation can be implemented by using a vacuum pump on that same exhaust point.

Therefore, during initialization, the vaporization section 59, the precipitator section 26, and other parts of the system 100 are charged with Argon gas when the rotatable precipitator electrode 38 is rotating, to pump the Argon gas around both the precipitator section 26 and the vaporization section 59. The pressure relief valve 70 (which may be electromagnetically assisted with a control signal from the process controller 18) is at the highest physical point in the system, and at a pressure setting that exhausts from the bypass annulus 55 through an exhaust cavity as the system 100 fills, venting off the air first (Argon gas is heavier than air).

During operation at certain vapor temperatures where toxic vapors are known to exist, the Argon gas supply is activated to the bypass annulus 55 to increase pressure and therefore cause exhausting of toxic vapors through the pressure relief valve 70 and then expelled from the gas path exhaust conduit 8 (not shown here). Exhausting will also occur due to increasing pressure as the temperature ramps up between specific specified vaporization temperature set points as a result of gas expansion.

In an example embodiment, a discharge detector or electrical energy sensor 62 is used to detect a discharge and produce a signal discharge detected 54. The tendency for electrostatic discharges as a result of avalanche effects in relatively pure Argon gas is used to detect and use the discharge detected signal 54 the completion of the vaporization process at any given temperature, where under conditions of low vapor content the electrical gap between a pair of electrical contacts set at a specific distance (not shown) will break down causing a discharge when relatively vapor free Argon is flowing into the precipitator section 26. A discharge detector generates a control signal (the discharge detected signal 54) to signal the process controller 18 to increment to the next specified temperature value. In some examples, the discharge detector can be an electrical energy sensor 62 such as a voltage sensor and/or a current sensor. In other examples, other sensors and controllers (not shown) are used to determine that there are no more compounds with the Argon gas, and that the heat source 19 is to proceed to the next highest specified temperature value.

In some examples, monitoring and/or controlling of the current and/or voltage of the rotatable precipitator electrode 38 can be performed by the process controller 18. A control signal can be used by the process controller 18 to represent the vapor density as a proportional analog signal. An electrical energy sensor 62 such as a current sensor or a voltage sensor can be used in some examples to detect the current or voltage, respectively.

The Argon ionization potential as a pure gas will have a relatively low value, which will increase in the presents of vapors, and can be used to both indicate when a particular temperature vaporized compound is substantially exhausted from the feed materials, to signal the next temperature point to be processed.

In some examples, the process controller 18 can use this proportional analog signal to map the temperatures where the maximum vapor flow is obtained. In an example, the proportional analog signal is used by the process controller 18 for characterization of specific compound content of one feedstock versus a different feedstock at all temperatures used in the process.

In example embodiments, the configuration of the ionization source allows closed loop control of the current by automatic adjustment of the voltage, which allows effective measurement of the impedance of the ionization cavity, which is akin to how many common ionization type smoke detectors function. Changes in the ion current in a common smoke detector are used to detect smoke in the ion chamber, smoke particles have a higher mass than the ionized gas molecules thus when an ionized gas molecule sticks to a much more massive smoke particle the $mv^2$ remaining constant (proportional to temperature=$½ mv^2$, where m=Mass, v=Velocity) the Velocity of the combined particles are much slower, thus the drift current (formed by the ions flowing to the charged plates or in our case the precipitation target electrode) reaching the detector is reduced.

In this configuration, the fixed ion current is set by the process controller 18 at a non avalanche level (non arcing) with 100% Argon content (no vapor), to provide a certain specified voltage across the ionization chamber (the rotating centrifugal electrostatic precipitator 38), which will then become a function of the ratio of Vapor/Argon, since the voltage will increase as the current tends to decrease, to hold the current constant. As the mean free particle velocity reduces due to the increase in mass in the chamber, the increase in voltage is expected to be proportional to the increase in particle mass in the chamber.

This is used for a number of potential purposes such as detecting when most of the vapor (e.g., above a threshold) has been processed at any given temperature, thus signaling the next temperature step in the process.

In some examples, the collected vapor data versus temperature is used by the process controller 18 or an external computer to determine specific grades of feedstock over time.

The specified temperature value is a fixed temperature value in some examples. In other examples, the specified temperature is a specified temperature range instead of a fixed temperature value. For example, a specified temperature range can be selected by the process controller 18 such that the minimum temperature value is the vaporization temperature of one compound of the botanical material 1 and the maximum temperature value of the temperature range is any amount that is less than the next highest vaporization temperature of the next compound in the botanical material 1. In some example embodiments, the temperature of the vaporization section 59 can be controlled to periodically oscillate or otherwise vary within the temperature range. In some example embodiments, the temperature of the vaporization section 59 can be controlled to gradually increase form the minimum temperature value to the maximum temperature value of the temperature range, until that particular compound of the botanical material 1 is vaporized and precipitated and collected. The specified temperature value selected by the process controller 18 can also be dependent on the present pressure or an automatically controlled pressure of the vaporization section 59. The specified temperature value may require adjustment while in the processing of vaporizing a particular compound, to account for any changes in the present pressure of the vaporization section 59.

Figure 10:
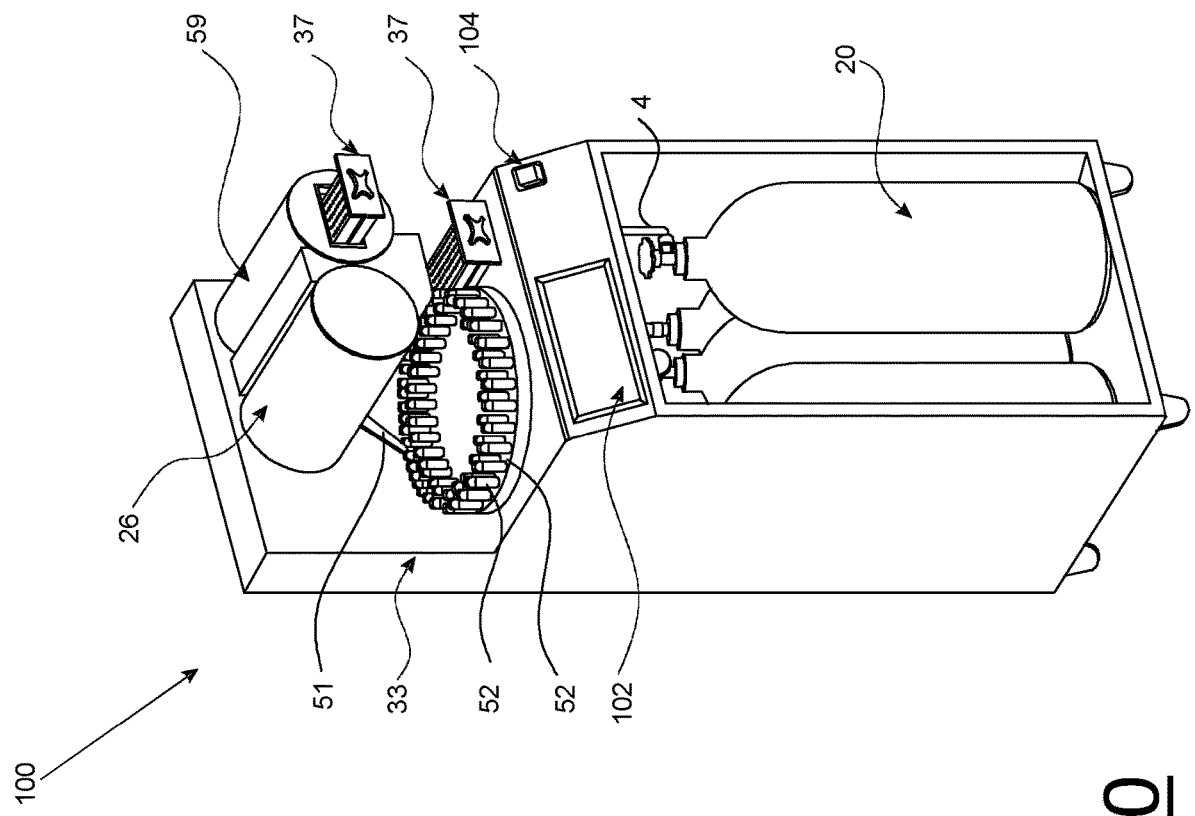
FIG. 10 is a perspective view of an example embodiment of a physical version of the botanical extraction system.
Figure 11:
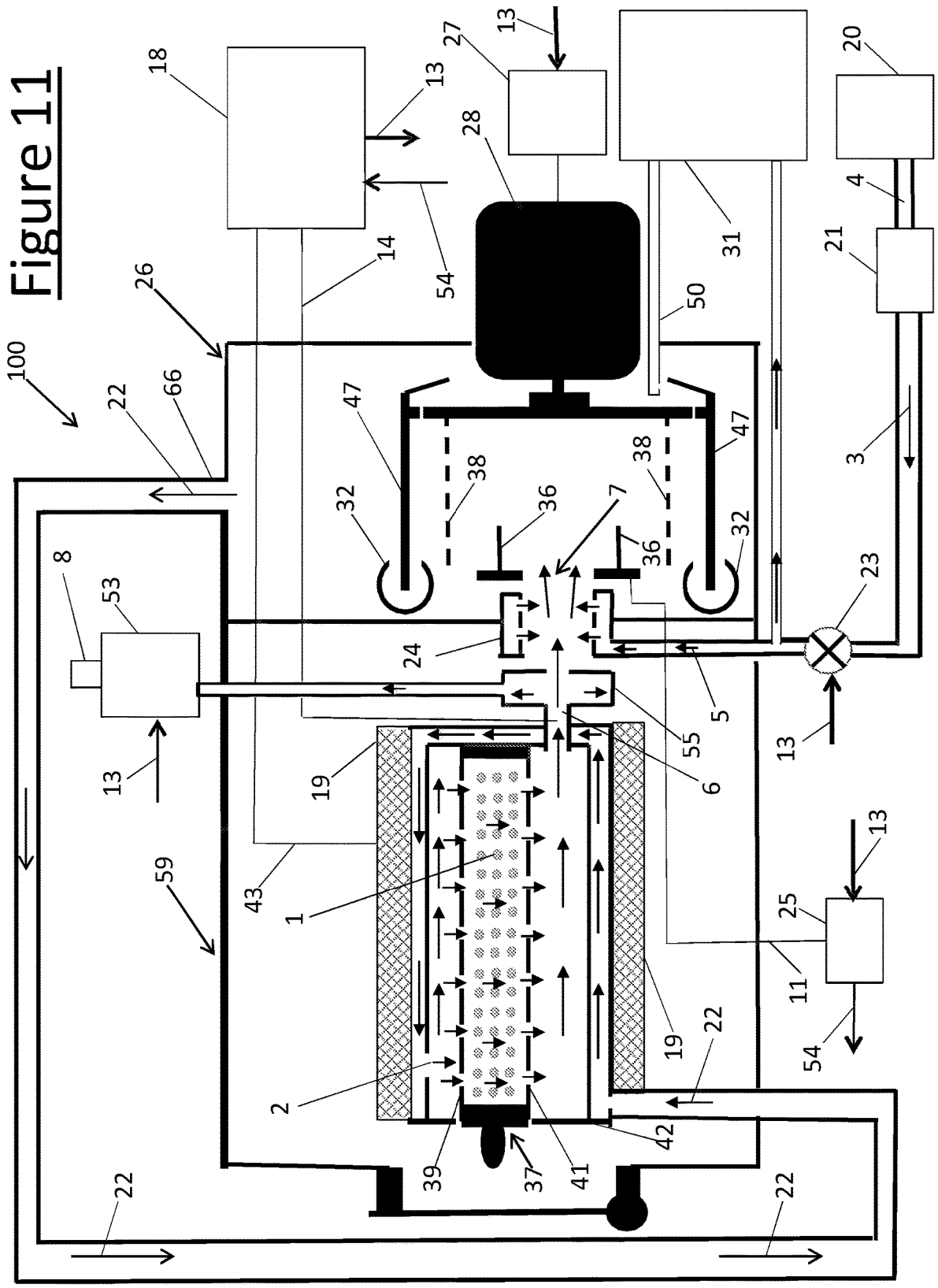
FIG. 11 is a schematic diagram of a fifth example embodiment of a botanical extraction system including an Argon gas recirculating system.

FIG. 10 is a perspective view of an example embodiment of a physical version of the system 100. A touch screen 102 can be used as a user interface for outputting (displaying) information and for receiving information from the user. In some examples, the specific type of botanical material 1 is selected by way of the touch screen 102, and the specific temperature values for specific time durations and selected from preprogrammed settings for that specific type of botanical material 1. Other example user input devices include a remote control, mobile phone or computer application, control panel, etc. A hard button 104 or suitable switch can be used for turning on and off the entire system 100. The drawer type cartridge 37 can have a generally rectangular prism shaped frame formed of metal, having the top containment screen 39 and the bottom containment screen 41, and can have a handle as shown. In FIG. 10, one drawer type cartridge 37 is shown partially inserted into the vaporization section 59, and another drawer type cartridge 37 is shown as a spare. Each drawer type cartridge 37 can be filled on-demand by the user in some examples, and in other examples can be pre-packaged by the manufacturer. Each drawer type cartridge 37 can be recycled after use by way of cleaning and refilling. In some examples, not shown, each drawer type cartridge 37 can be automatically processed in sequence by the system 100, wherein each drawer type cartridge 37 can be automatically inserted into the vaporization section 59, processed to sequentially extract the each of the one or more compounds, and removed, followed by automatic insertion and processing of the next drawer type cartridge 37. The Argon supply 20 can be stored in one or more tanks, as shown in FIG. 10.

In some examples, the system 100 is at a small scale as a home kitchen type appliance or can be scaled up to any larger size for industrial production or processing. In some examples, the system 100 is not necessarily limited to the application described and could be applied to other botanical materials or other oil fractionation applications. The oil may be contained by materials other than botanical materials, which can be provided to the system for solvent-less vaporization, extraction, and fractionation of the oils or compounds in the same way as described above for botanical materials. Other gases besides Argon may be used for the same or different purposes.

In some examples, the process controller 18 of the system 100 can interface with the user by way of a user interface. Examples of the user interface include the touch screen 102, display screen, microphone, speaker, buttons, keyboard or keypad. Interaction with the user can also be made using a second device, such as a mobile phone, mobile tablet, personal computer, or a home smart speaker assistant such as Amazon Echo™, Apple HomePod™, or Google Home™. A communication subsystem can be included in the system 100 to perform wireless or wired communication. The power supply 25 for the system 100 can be a battery, a DC power interface such as Universal Serial Bus (USB) and/or an A/C power converter with plug.

Other suitable liquids may be substituted for the distilled water as required or for different or additional purposes.

The exhaust gases may be further processed or filtered in a separate similar or different system for recycling or for any other purpose or reason.

In some example embodiments, the described system 100 and processes can be implemented to collect the respective one or more compounds in a batch process, for example using the drawer type cartridge 37 for each batch. In other examples, example embodiments of the described system 100 and processes can be implemented in a continuous batch process.

FIG. 15 is a flow diagram for a method 1500 of extracting botanical oils from a botanical material 1 without the use of a solvent, using the system 100 in accordance with example embodiments. In examples, the method 1500 can be controlled by the process controller 18 and/or the controller 30. Steps of the method 1500 are sequentially performed for each one or more compounds of the botanical material 1. At step 1502, the method 1500 includes vaporizing, using the heat source 19 (heater), the botanical material 1 at a specified temperature value. In the sequence, each specified temperature value causes a respective vaporization temperature of the desired one or more of the compounds in the botanical material 1 to result in respective vaporized one or more compounds. At step 1504, the method 1500 includes aerosolizing, using an inert gas (e.g. Argon gas 5), the respective vaporized one or more compounds into respective aerosolized one or more compounds. At step 1506, the method includes charging, using one or more of the corona electrodes 36, the respective aerosolized one or more compounds. At step 1508, the method includes precipitating, within an interior of the rotatable precipitator electrode 38 (comprising a frame having a metal screen), the respective charged aerosolized one or more compounds into respective precipitated one or more compounds, by rotating the frame using the motor 28. At step 1510, the method includes collecting, using the collection system 29, the respective precipitated one or more compounds that are externally centrifugally expelled from the rotatable precipitator electrode 38 when the rotatable precipitator electrode 38 is rotated. At step 1512, the steps of the method 1500 are repeated for the next one or more compounds in the botanical material 1. The method 1500 is repeated until all of the compounds in the botanical material 1 are processed, or other suitable automated, sensed, or controlled events. In some examples, at step 1514, the method 1500 includes bypassing the processing of unwanted one or more vaporized compounds within the sequence by exhausting the unwanted one or more vaporized compounds from an exhaust outlet (e.g. the bypass annulus 55 and associated exhaust cavity). Such unwanted one or more vaporized compounds are not aerosolized, charged, precipitated or collected.

An example embodiment is a system for extracting compounds from botanical material, comprising: a heater for sequentially vaporizing the botanical material at specified temperature values, each specified temperature value causing a respective vaporization temperature of one or more of the compounds in the botanical material to result in respective vaporized one or more compounds; a gas inlet for receiving an inert gas, the inert gas being for sequentially aerosolizing each of the respective vaporized one or more compounds into respective aerosolized one or more compounds; a corona electrode for sequentially charging each of the respective aerosolized one or more compounds; an electrostatic precipitator including a frame having a metal screen and the metal screen defines an interior for receiving and sequentially precipitating each of the respective charged aerosolized one or more compounds into respective precipitated one or more compounds, a motor for controlling rotation the frame having the metal screen around an axis of rotation to perform said precipitating; and a collection system at least part of which is positioned radially exterior from the frame having the metal screen with respect to the axis of rotation, the collection system for sequentially collecting each of the respective precipitated one or more compounds for each specified temperature value that are externally centrifugally expelled from the frame having the metal screen when the frame is rotated.

In an example embodiment, the inert gas is Argon gas.

In an example embodiment, the inert gas is unheated when introduced for the aerosolizing of each of the respective vaporized one or more compounds.

In an example embodiment, the system further comprises a second gas inlet for introducing a second inert gas to the botanical material during the vaporizing of the botanical material.

In an example embodiment, the second inert gas and the second gas inlet are heated by the heater to a temperature that is greater than each respective specified temperature value of the respective one or more compounds.

In an example embodiment, the system further comprises one or more temperature sensors for detecting temperature of the respective vaporized one or more compounds, wherein the heater is controlled to, based on the detected temperature, heat the second gas inlet and the second inert gas to achieve the temperature that is greater than each respective specified temperature value of the respective one or more compounds.

In an example embodiment, the system further comprises a pressure regulator for pressurizing the second inert gas prior to the introducing to the botanical material.

In an example embodiment, the second inert gas is Argon gas.

In an example embodiment, the vaporizing of the botanical material is performed without a liquid solvent or liquid solvents.

In an example embodiment, the precipitating of the respective charged aerosolized one or more compounds is performed without a liquid solvent or liquid solvents.

In an example embodiment, the system further comprises an activatable bypass for removing unwanted vaporized one or more compounds that are vaporized by the heater without the aerosolizing and without the precipitating.

In an example embodiment, flow of the inert gas, the corona electrode, and/or the motor are deactivated when the activatable bypass is activated.

In an example embodiment, the removing by the bypass is controlled to be performed without the receiving by the interior of the frame.

In an example embodiment, the activatable bypass is controlled to be activated at one or more specified temperature values, at 0.05 mmHg, of i) less than 52 Degrees C., or ii) greater than 180 Degrees C., or iii) on or about 110.6 Degrees C. for Toluene, or any of i), ii), or iii) adjusted for present pressure as compared to 0.05 mmHg.

In an example embodiment, the system further comprises a pressure relief valve for limiting a maximum pressure of a pressure of the system.

In an example embodiment, the pressure relief valve is configured for removing unwanted contaminants or vaporized one or more compounds that are vaporized by the heater.

In an example embodiment, the inert gas is controlled to be inserted through the gas inlet or a second gas inlet to cause activation of the pressure relief valve.

In an example embodiment, the system further comprises a circuit for recirculating the inert gas that are externally centrifugally expelled from the frame having the metal screen and having the one or more compounds electrostatically cleaned from the inert gas by the electrostatic precipitator.

In an example embodiment, the system further comprises one or more paddle type vanes at the electrostatic precipitator which rotate from control by the motor for facilitating the recirculating of the inert gas.

In an example embodiment, each specified temperature value is a specified fixed temperature value.

In an example embodiment, each specified temperature value is a specified range of temperature values.

In an example embodiment, each specified range of temperature values has a minimum temperature value which is a minimum respective vaporization temperature of the respective one or more of the compounds and has a maximum temperature value which is less than the respective vaporization temperature of a next highest vaporization temperature of a next one or more compounds in the botanical material.

In an example embodiment, the collection system comprises a removable sleeve for adsorbing the respective precipitated one or more compounds.

In an example embodiment, the collection system comprises a movable belt of material for adsorbing the respective precipitated one or more compounds.

In an example embodiment, the collection system further comprises: a rotatable sleeve positioned radially exterior from the frame having the metal screen with respect to the axis of rotation, the rotatable sleeve rotatable along the axis of rotation, the rotatable sleeve having a first end and an opposite second end generally across the axis of rotation; and a conduit for flow of a fluid that flows from the first end of the rotatable sleeve to the second end of the rotatable sleeve for transporting the respective precipitated one or more compounds.

In an example embodiment, the rotatable sleeve is mounted to the motor.

In an example embodiment, the collection system further comprises a conveyor and collection vessels supported by the conveyor, each collection vessel for individually collecting each of the respective precipitated one or more compounds with the fluid.

In an example embodiment, the fluid is distilled water.

In an example embodiment, the metal screen defines apertures of a size to permit passage of the respective precipitated one or more compounds.

In an example embodiment, the metal screen includes an interior metal screen having a fine metal mesh and an exterior metal screen having a coarse metal mesh as compared to the fine metal mesh.

In an example embodiment, the frame having the metal screen is generally cylindrical.

In an example embodiment, the axis of rotation is generally horizontal and an opening to the interior of the frame having the metal screen is defined at one lateral side of the frame for the receiving of each of the respective charged aerosolized one or more compounds.

In an example embodiment, the system further comprises a circuit for recirculating the inert gas from the frame having the metal screen, the inert gas being recirculated to the gas inlet.

In an example embodiment, the heater causes each of the specified temperature values in an increasing sequential order.

In an example embodiment, the system further comprises a detector for determining presence of the inert gas without any of the one or more compounds, and in response the heater is controlled to achieve a next specified vaporization temperature of a next one or more compounds in the botanical material.

In an example embodiment, the system further comprises a discharge detector for detecting a discharge resulting from presence of the inert gas without any of the one or more compounds or below a threshold of the one or more compounds, and in response the heater is controlled to achieve a next specified vaporization temperature of a next one or more compounds in the botanical material.

In an example embodiment, the system further comprises a cartridge including sidewalls for containing the botanical material, at least one of the walls comprising a screen for permitting output of the respective vaporized one or more compounds.

In an example embodiment, the botanical material comprises milled botanical material.

In an example embodiment, the botanical material comprises cannabis botanical material.

In an example embodiment, any one of the specified temperature values comprises any one of, at 0.05 mmHg:

52 Degrees C. for vaporizing Cannabigerol (CBG), or

119 Degrees C. for vaporizingg Beta-Caryophyllene, or

134 Degrees C. for vaporizing Beta-Siteosterol, or

157 Degrees C. for vaporizingg Delta-9-Tetrahydrocannabinol (THC), or anywhere in a range of 160-180 Degrees C. for vaporizing Cannabidiol (CBD); or wherein any one of the specified temperature values comprises any of the above specified temperature values at 0.05 mmHg adjusted for present pressure as compared to 0.05 mmHg.

In an example embodiment, the specified temperature values comprise the following at 0.05 mmHg, or adjusted for present pressure as compared to 0.05 mmHg, in sequence for the sequentially vaporizing:

52 Degrees C. for vaporizing Cannabigerol (CBG),
119 Degrees C. for vaporizing Beta-Caryophyllene,
134 Degrees C. for vaporizing Beta-Siteosterol,
157 Degrees C. for vaporizing Delta-9-Tetrahydrocannabinol (THC), and
anywhere in a range of 160-180 Degrees C. for vaporizing Cannabidiol (CBD).

In an example embodiment, the system further comprises at least one controller for controlling the heater, flow of the inert gas, the corona electrode, the motor, and the collection system.

In an example embodiment, the system is configured to collect each respective one or more compounds in a batch process.

In an example embodiment, the collection system is controlled to individually collect each of the respective precipitated one or more compounds for each specified temperature value.

In an example embodiment, the system further comprises a sensor used to determine conductivity due to an amount of the inert gas versus the respective aerosolized one or more compounds, wherein when the determined conductivity indicates that there is not any of the respective aerosolized one or more compounds or below a threshold amount of the respective aerosolized one or more compounds, the heater is controlled to achieve a next specified vaporization temperature of a next one or more compounds in the botanical material.

In an example embodiment, when the metal screen is performing the precipitating, the metal screen is grounded, or controlled to be at zero volts, or controlled to be at a voltage that is different than a charge provided by the corona electrode.

An example embodiment is method for extracting compounds from botanical material, comprising: sequentially vaporizing, using a heater, the botanical material at specified temperature values, each specified temperature value causing a respective vaporization temperature of one or more of the compounds in the botanical material to result in respective vaporized one or more compounds; for each of the vaporized one or more compounds from each specified temperature value: aerosolizing, using an inert gas, the respective vaporized one or more compounds into respective aerosolized one or more compounds, charging, using a corona electrode, the respective aerosolized one or more compounds, precipitating, within an interior of a metal screen of a frame, the respective charged aerosolized one or more compounds into respective precipitated one or more compounds, by rotating the frame using a motor, and collecting the respective precipitated one or more compounds that are externally centrifugally expelled from the frame having the metal screen when the frame is rotated.

In example embodiments, as appropriate, each illustrated block or module may be combined in some example embodiments, and more or less blocks or modules may be present in other example embodiments. Furthermore, some of the blocks or modules may be separated into a number of sub-blocks or sub-modules in other embodiments.

While some of the present embodiments are described in terms of methods, a person of ordinary skill in the art will understand that present embodiments are also directed to various apparatus such as a device or system including components for performing at least some of the aspects and features of the described methods, be it by way of hardware components, software or any combination of the two, or in any other manner. Moreover, an article of manufacture for use with the apparatus, such as a pre-recorded storage device or other similar non-transitory computer readable medium including program instructions recorded thereon, or a computer data signal carrying computer readable program instructions may direct an apparatus to facilitate the practice of the described methods. It is understood that such apparatus, articles of manufacture, and computer data signals also come within the scope of the present example embodiments.

While some of the above examples have been described as occurring in a particular order, it will be appreciated to persons skilled in the art that some of the messages or steps or processes may be performed in a different order provided that the result of the changed order of any given step will not prevent or impair the occurrence of subsequent steps. Furthermore, some of the messages or steps described above may be removed or combined in other embodiments, and some of the messages or steps described above may be separated into a number of sub-messages or sub-steps in other embodiments. Even further, some or all of the steps of the conversations may be repeated, as necessary. Elements described as methods or steps similarly apply to systems or subcomponents, and vice-versa.

In example embodiments, the one or more controllers can be implemented by or executed by, for example, one or more of the following systems: Personal Computer (PC), Programmable Logic Controller (PLC), microprocessor, cloud computing, server (local or remote), mobile phone or mobile communication device.

The term "computer readable medium" as used herein includes any medium which can store instructions, program steps, or the like, for use by or execution by a computer or other computing device including, but not limited to: magnetic media, such as a diskette, a disk drive, a magnetic drum, a magneto-optical disk, a magnetic tape, a magnetic core memory, or the like; electronic storage, such as a random access memory (RAM) of any type including static RAM, dynamic RAM, synchronous dynamic RAM (SDRAM), a read-only memory (ROM), a programmable-read-only memory of any type including PROM, EPROM, EEPROM, FLASH, EAROM, a so-called "solid state disk", other electronic storage of any type including a charge-coupled device (CCD), or magnetic bubble memory, a portable electronic data-carrying card of any type including COMPACT FLASH, SECURE DIGITAL (SD-CARD), MEMORY STICK, and the like; and optical media such as a Compact Disc (CD), Digital Versatile Disc (DVD) or BLU-RAY® Disc.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art having the benefit of the present disclosure, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive.

NUMERICAL DESIGNATIONS

1 Botanical material
2 Gas inlet
3 Regulated Argon gas
4 High pressure Argon gas
5 Argon gas
6 Exit vapor (hot oil vapor and hot Argon)
7 Aerosolized oil and Argon
8 Gas path exhaust conduit
9 Centrifugal rotational drive
10 Drive motor control signal
11 Electrostatic power supply
12 Liquid oil droplets
13 Control signal
14 Temperature (First section vapor exit temperature)
15 Control signal
16 Distributor control
18 Process controller
19 Heat Source
20 Argon supply
21 Argon pressure regulator
22 Argon gas
23 Solenoid valve
24 Mixer section
25 Power supply
26 Precipitator section
27 Motor drive control
28 Motor
29 Collection system
30 Controller
31 Fluid supply
32 Annular fluid conduit
33 Collection vessel indexing system
34 Product
35 Separated product
36 Corona electrodes
37 Cartridge
38 Rotatable precipitator electrode
39 Upper containment screen
40 Support system
41 Lower containment screen
42 Semi-sealed oven enclosure
43 Heater control
44 Removable sleeve
45 Belt support sleeve
46 Moveable belt
47 Rotatable sleeve
48 Distilled water or other fluid film
49 Distilled water or other fluid plus compound
50 Conduit
51 Drain conduit
52 Collection vessel
53 Bypass duct
54 Discharge detected signal
55 Vapor bypass intake annulus
58 Conveyor
59 Vaporization section
60 Centrifugal electrostatic precipitator
62 Electrical energy Sensor
64 Temperature Sensor
66 Recirculation conduit
68 Tangential gas duct
70 Pressure Relief Valve
72 Paddle type vane
74 Mount
76 Vane
80 Heat sink tube
100 System
102 Touch screen
104 Hard button

What is claimed is:

1. A system for botanical material, comprising:
a gas inlet for receiving an inert gas, the inert gas being for aerosolizing respective vaporized one or more compounds of the botanical material into respective aerosolized one or more compounds;
a corona electrode for charging the respective aerosolized one or more compounds;
an electrostatic precipitator including a frame which defines an interior for receiving and precipitating the respective charged aerosolized one or more compounds into respective precipitated one or more compounds, and a motor for controlling rotation of the frame around an axis of rotation to perform said precipitating; and
a collection system at least part of which is positioned radially exterior from the frame with respect to the axis of rotation, the collection system for collecting the respective precipitated one or more compounds that are externally centrifugally expelled from the frame when the frame is rotated.

2. The system as claimed in claim 1, wherein the inert gas is unheated when introduced for the aerosolizing the vaporized one or more compounds.

3. The system as claimed in claim 1, further comprising a second gas inlet for introducing a second inert gas to the botanical material during the aerosolizing respective vaporized one or more compounds of the botanical material into respective aerosolized one or more compounds.

4. The system as claimed in claim 3, further comprising a heater configured to heat the second inert gas and the second gas inlet to a temperature that is greater than a vaporization temperature of at least one of the one or more compounds of the botanical material.

5. The system as claimed in claim 4, further comprising one or more temperature sensors for detecting temperature of the respective vaporized one or more compounds, wherein the heater is controlled to heat, based on the detected temperature, to achieve the temperature that is greater than a vaporization temperature of the at least one of the one or more compounds of the botanical material.

6. The system as claimed in claim 3, further comprising a pressure regulator for pressurizing the second inert gas prior to the introducing to the botanical material.

7. The system as claimed in claim 3, wherein the second inert gas is Argon gas.

8. The system as claimed in claim 1, wherein the vaporizing of the botanical material is performed without a liquid solvent or liquid solvents.

9. The system as claimed in claim 1, wherein the precipitating of the respective charged aerosolized one or more compounds is performed without a liquid solvent or liquid solvents.

10. The system as claimed in claim 1, further comprising an activatable bypass for removing unwanted vaporized one or more compounds without the aerosolizing and without the precipitating.

11. The system as claimed in claim 10, wherein flow of the inert gas, the corona electrode, and/or the motor are deactivated when the activatable bypass is activated.

12. The system as claimed in claim 10, wherein the removing by the bypass is controlled to be performed without the receiving by the interior of the frame.

13. The system as claimed in claim 1, further comprising a pressure relief valve for limiting a maximum pressure of a pressure of the system.

14. The system as claimed in claim 13, wherein the pressure relief valve is configured for removing unwanted contaminants or vaporized one or more compounds of the botanical material.

15. The system as claimed in claim 14, wherein the inert gas is controlled to be inserted through the gas inlet to cause activation of the pressure relief valve.

16. The system as claimed in claim 1, further comprising a circuit for recirculating the inert gas that are externally centrifugally expelled from the frame and having the one or more compounds electrostatically cleaned from the inert gas by the electrostatic precipitator.

17. The system as claimed in claim 16, further comprising one or more paddle type vanes at the electrostatic precipitator which rotate from control by the motor for facilitating the recirculating of the inert gas.

18. The system as claimed in claim 1, wherein the collection system further comprises:
a conduit for flow of a fluid for transporting the respective precipitated one or more compounds.

19. The system as claimed in claim 18, wherein the collection system further comprises a conveyor and collection vessels supported by the conveyor, each collection vessel for individually collecting each of the respective precipitated one or more compounds with the fluid.

20. The system as claimed in claim 1, wherein the frame has a metal screen, wherein the metal screen defines apertures of a size to permit passage of the respective precipitated one or more compounds.

21. The system as claimed in claim 1, wherein the frame has a metal screen, wherein the metal screen includes an interior metal screen having a fine metal mesh and an exterior metal screen having a coarse metal mesh as compared to the fine metal mesh.

22. The system as claimed in claim 1, wherein the frame is generally cylindrical.

23. The system as claimed in claim 1, further comprising a circuit for recirculating the inert gas from the frame, the inert gas being recirculated to the gas inlet.

24. The system as claimed in claim 1, further comprising a cartridge including sidewalls for containing the botanical material, at least one of the sidewalls comprising a screen for permitting output of the respective vaporized one or more compounds.

25. The system as claimed in claim 1, further comprising at least one controller for controlling flow of the inert gas, the corona electrode, the motor, and the collection system.

26. The system as claimed in claim 1, wherein the frame has metal, wherein when the frame is performing the precipitating, the metal is grounded, or controlled to be at zero volts, or controlled to be at a voltage that is different than a charge provided by the corona electrode.

27. The system as claimed in claim 1, wherein the collection system further comprises collection vessels, each collection vessel for individually collecting each of the respective precipitated one or more compounds.

28. The system as claimed in claim 1, wherein the collection system further comprises one or more collection vessels for collecting the precipitated one or more compounds, wherein one of the collection vessels is for collecting at least two of the respective precipitated one or more compounds.

29. The system as claimed in claim 1, wherein the botanical material includes one or more botanical oils, wherein the respective vaporized one or more compounds of the botanical material include respective vaporized one or more botanical oils.

* * * * *